United States Patent
Nakagaki et al.

(10) Patent No.: US 11,054,381 B2
(45) Date of Patent: Jul. 6, 2021

(54) GAS SENSOR

(71) Applicant: NGK INSULATORS, LTD., Aichi (JP)

(72) Inventors: Kunihiko Nakagaki, Nagoya (JP); Taku Okamoto, Nagoya (JP); Osamu Nakasone, Inabe (JP); Nobukazu Ikoma, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 142 days.

(21) Appl. No.: 16/438,524

(22) Filed: Jun. 12, 2019

(65) Prior Publication Data
US 2019/0383766 A1    Dec. 19, 2019

(30) Foreign Application Priority Data

Jun. 15, 2018 (JP) .............................. JP2018-114319

(51) Int. Cl.
| | |
|---|---|
| *G01N 27/406* | (2006.01) |
| *F01N 11/00* | (2006.01) |
| *G01N 27/41* | (2006.01) |
| *G01N 27/416* | (2006.01) |
| *G01N 27/409* | (2006.01) |
| *F01N 3/20* | (2006.01) |

(52) U.S. Cl.
CPC ......... *G01N 27/4067* (2013.01); *F01N 3/208* (2013.01); *F01N 11/007* (2013.01); *G01N 27/409* (2013.01); *G01N 27/41* (2013.01); *G01N 27/416* (2013.01); *F01N 2560/021* (2013.01); *F01N 2560/026* (2013.01); *F01N 2610/144* (2013.01)

(58) Field of Classification Search
None
See application file for complete search history.

(56) References Cited

U.S. PATENT DOCUMENTS

| | | | |
|---|---|---|---|
| 2009/0120791 A1* | 5/2009 | Miyashita | G01N 27/4077 204/412 |
| 2019/0128833 A1 | 5/2019 | Nakagaki | |

FOREIGN PATENT DOCUMENTS

WO    2017/222002 A1    12/2017

\* cited by examiner

*Primary Examiner* — J. Christopher Ball
(74) *Attorney, Agent, or Firm* — Mattingly & Malur, PC

(57) ABSTRACT

A first gas sensor includes a main pump cell that pumps oxygen inside a main oxygen concentration adjustment chamber, by applying a main pump voltage between a main interior side electrode and an exterior side electrode, and causing a main pump current to flow, a preliminary pump cell that pumps the oxygen inside a preliminary adjustment chamber by applying a preliminary pump voltage between an interior side preliminary electrode and the exterior side electrode, and causing a preliminary pump current to flow, and a constant control unit that controls the preliminary pump voltage of the preliminary pump cell in a manner so that the main pump current of the main pump cell becomes constant.

10 Claims, 20 Drawing Sheets

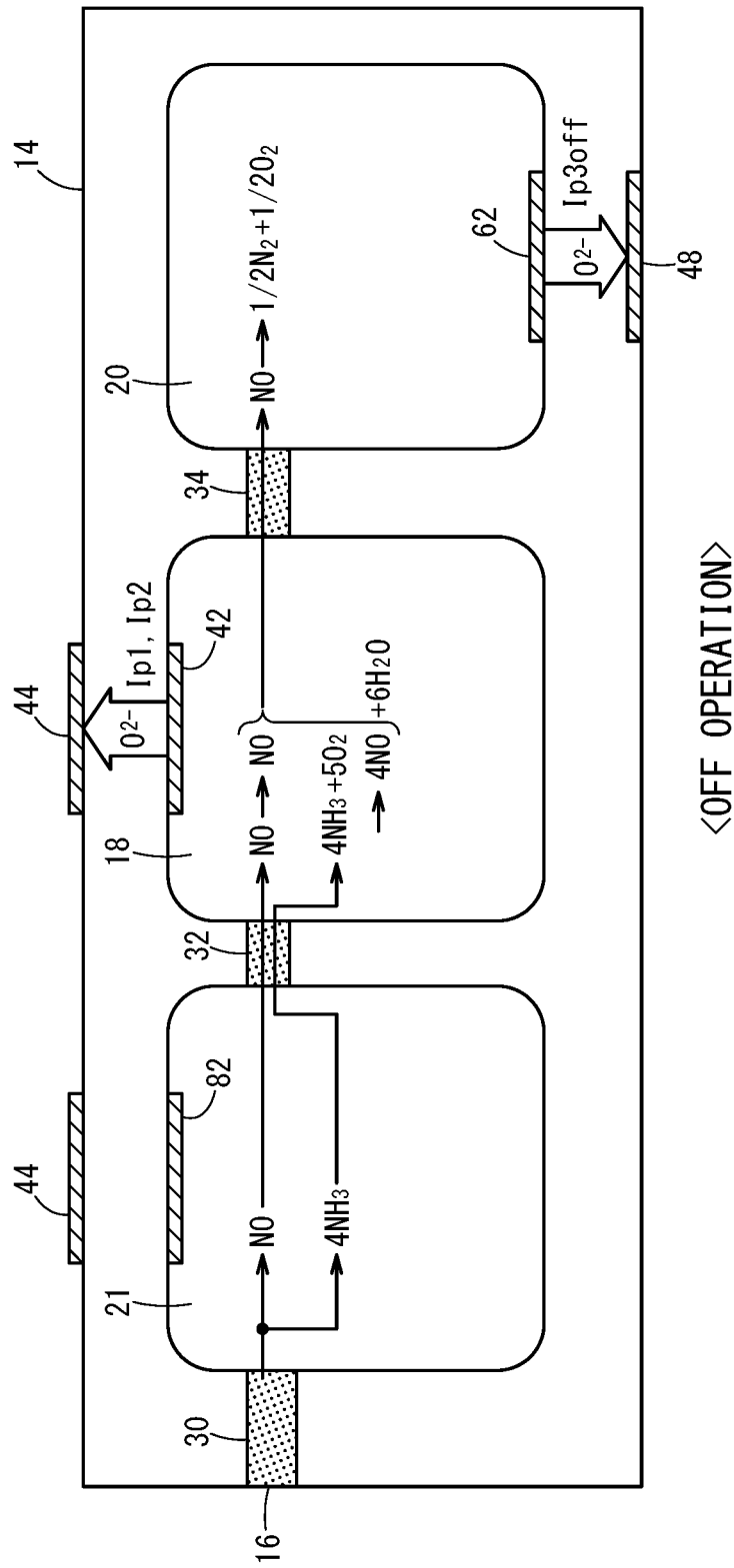

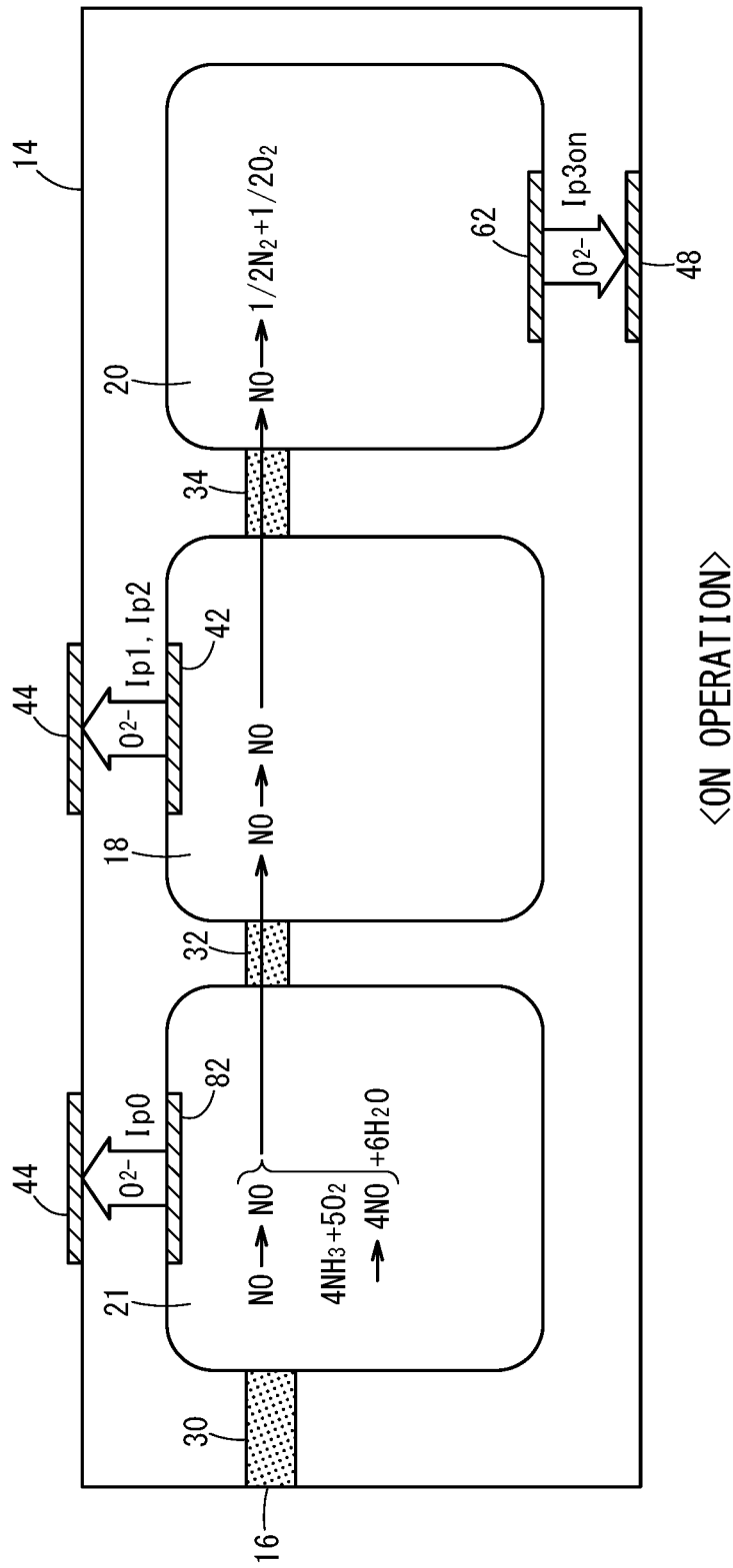

| O₂ [%] | Vp0 [V] |
|---|---|
| 1 | -0.10 |
| 5 | 0.35 |
| 10 | 0.60 |
| 20 | 0.85 |

RELATIONSHIP BETWEEN OXYGEN CONCENTRATION
O₂ (%) AND PRELIMINARY PUMP VOLTAGE Vp0

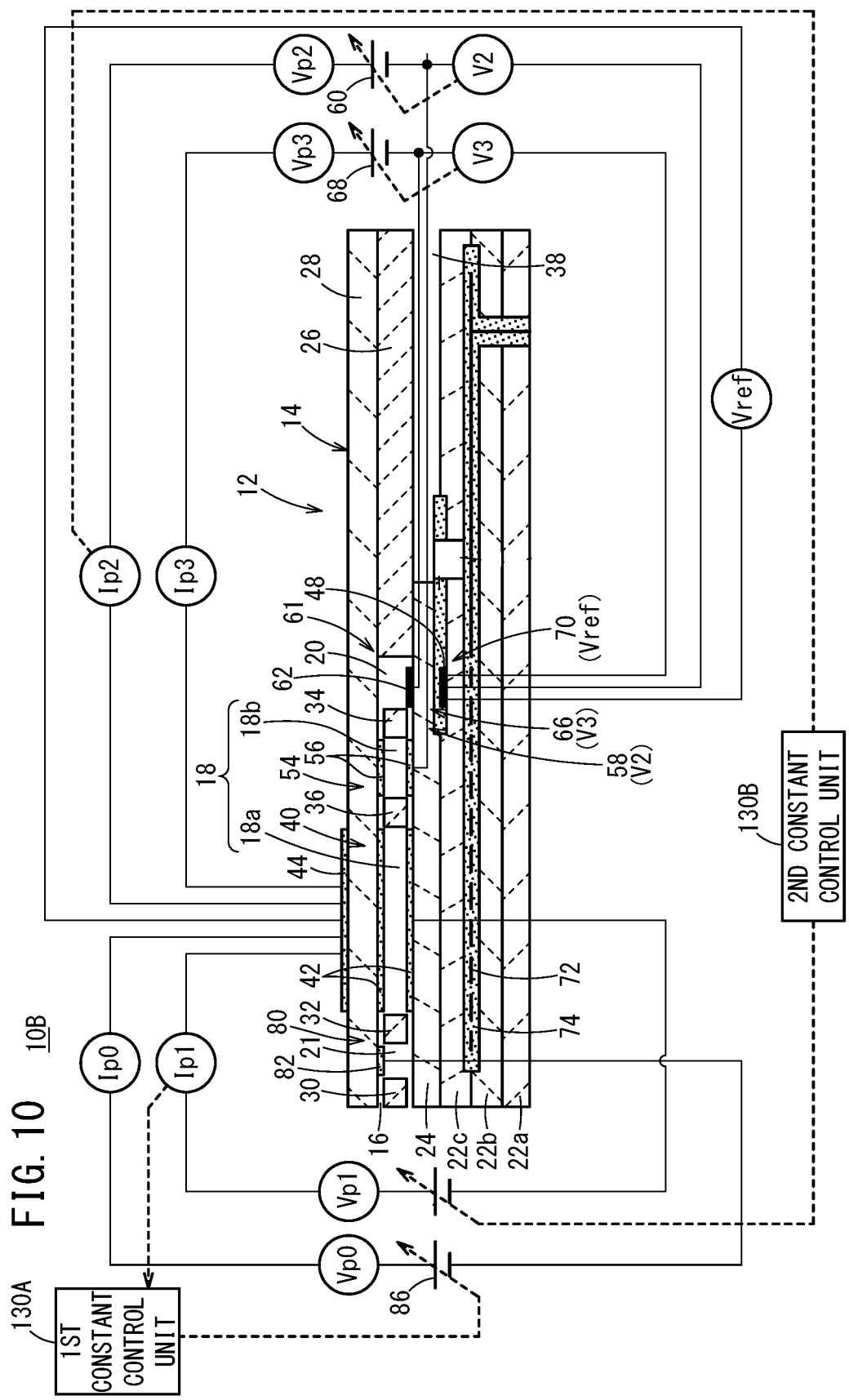

| O₂ [%] | Vp0 [V] |
|---|---|
| 1 | 0.235 |
| 5 | 0.47 |
| 10 | 0.587 |
| 20 | 0.794 |

RELATIONSHIP BETWEEN OXYGEN CONCENTRATION
$O_2$ (%) AND PRELIMINARY PUMP VOLTAGE Vp0

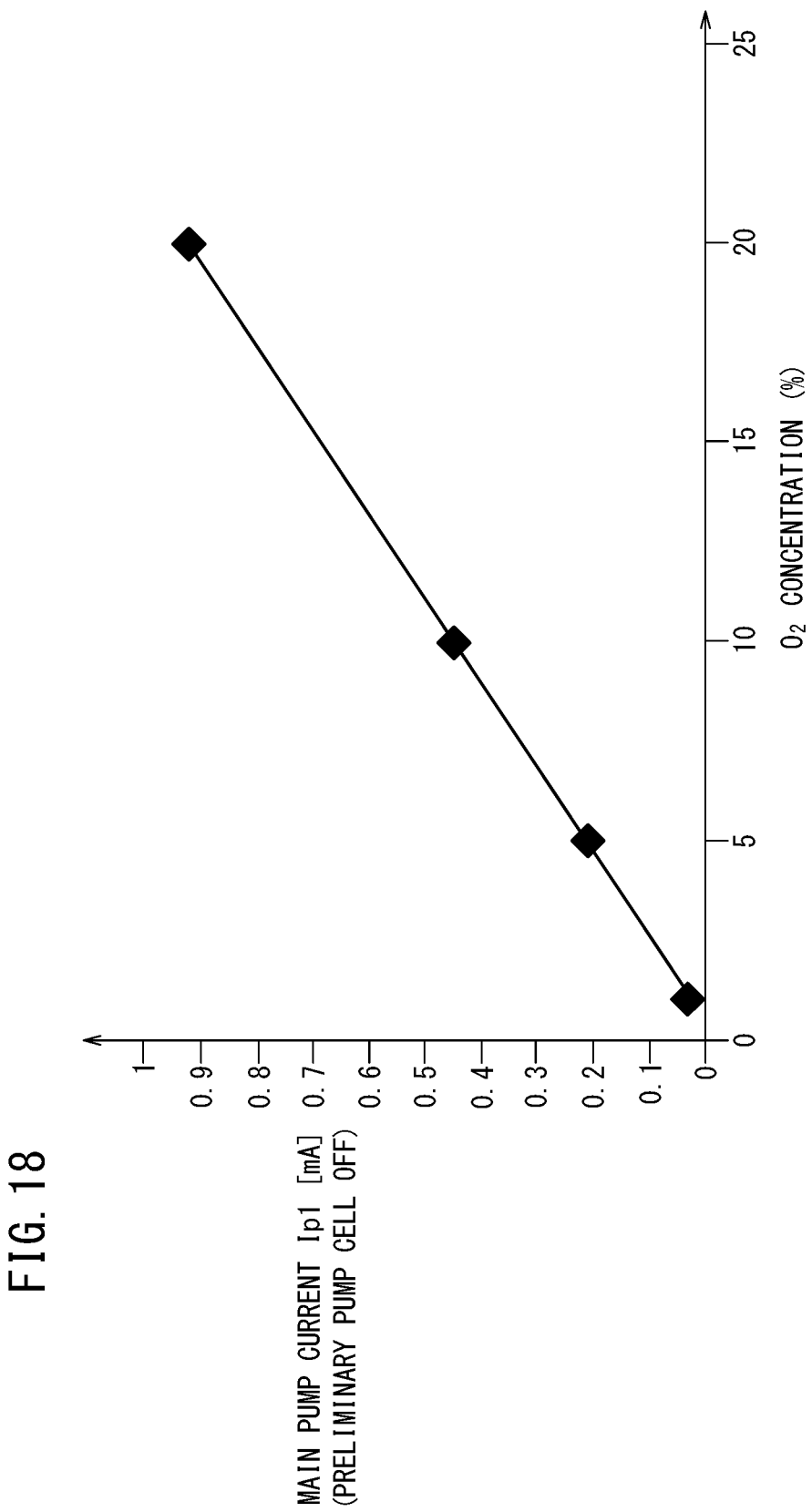

GAS SENSOR

CROSS-REFERENCE TO RELATED APPLICATION

This application is based upon and claims the benefit of priority from Japanese Patent Application No. 2018-114319 filed on Jun. 15, 2018, the contents of which are incorporated herein by reference.

BACKGROUND OF THE INVENTION

Field of the Invention

The present invention relates to a gas sensor, which is capable of measuring respective concentrations of a plurality of target components in a gas to be measured.

Description of the Related Art

International Publication No. WO 2017/222002 has the object of providing a gas sensor in which it is possible to accurately measure over a prolonged period the concentration of a non-combusted component such as exhaust gas, and a plurality of target components (for example, NO, $NH_3$, etc.) that coexist in the presence of oxygen.

In order to achieve this object, the gas sensor described in International Publication No. WO 2017/222002 includes a specified component measurement unit adapted to measure the concentration of a specified component in a measurement chamber, a preliminary oxygen concentration control unit adapted to control the oxygen concentration inside a preliminary adjustment chamber, and a drive control unit adapted to control driving and stopping of the preliminary oxygen concentration control unit. The gas sensor further includes a target component acquisition unit adapted to acquire concentrations of a first target component and a second target component, on the basis of a difference between sensor outputs from the specified component measurement unit at a time that the preliminary oxygen concentration control unit is driven and at a time that the preliminary oxygen concentration control unit is stopped, and one of the respective sensor outputs.

SUMMARY OF THE INVENTION

In the gas sensor described in International Publication No. WO 2017/222002, a space defined between a first diffusion rate control member of a gas inlet portion and an inwardly disposed second diffusion rate control member serves as a "preliminary adjustment chamber" with a preliminary adjustment electrode formed therein. In addition, by supplying ON and OFF signals to the preliminary adjustment electrode, the gas sensor performs pumping in and pumping out of oxygen into and out of the preliminary adjustment chamber.

Incidentally, the amount of oxygen flowing into the preliminary adjustment chamber is the largest among the plurality of empty chambers that constitute the gas sensor. For this reason, taking into consideration the fact that oxygen is pumped into and pumped out from the preliminary adjustment chamber, the pumping capacity of the preliminary adjustment chamber is required to be the most powerful.

However, in the gas sensor described in International Publication No. WO 2017/222002, it is understood that the volume of the preliminary adjustment chamber is small, and thus the pumping capacity thereof is small. Although under ordinary circumstances, the volume of the preliminary adjustment chamber may be increased, a problem results in that the size of the entire sensor element as a whole becomes increased.

Alternatively, there is also a method of increasing a first diffusion resistance, and thereby reducing the amount of gas that flows into the preliminary adjustment chamber. However, in accordance with such a method, the value of the sensor output also decreases, and there is a problem in that an improvement in the S/N ratio cannot be expected.

The present invention has been devised taking into consideration the aforementioned problems, and has the object of providing a gas sensor, which is capable of accurately measuring over a prolonged period of time the concentration of non-combusted components such as exhaust gas, and a plurality of components (for example, NO, $NH_3$, etc.) that coexist in the presence of oxygen, and in which, without being adversely influenced by the capacity of the preliminary adjustment chamber, it is possible to improve the S/N ratio of the sensor output, as well as to make the gas sensor smaller in scale.

[1] In a first aspect of a gas sensor according to the present invention, the gas sensor includes a sensor element including a structural body made up from a solid electrolyte that exhibits at least oxygen ion conductivity, a gas introduction port formed in the structural body and into which a gas to be measured is introduced, a main oxygen concentration adjustment chamber communicating with the gas introduction port, an auxiliary oxygen concentration adjustment chamber communicating with the main oxygen concentration adjustment chamber, a measurement chamber communicating with the auxiliary oxygen concentration adjustment chamber, and a preliminary adjustment chamber disposed between the gas introduction port and the main oxygen concentration adjustment chamber, and communicating with the gas introduction port, and further including a main oxygen concentration control unit configured to control the oxygen concentration inside the main oxygen concentration adjustment chamber, an auxiliary oxygen concentration control unit configured to control the oxygen concentration inside the auxiliary oxygen concentration adjustment chamber, a temperature control unit configured to control a temperature of the sensor element, a specified component measurement unit configured to measure a concentration of a specified component inside the measurement chamber, electrodes formed on an inner surface and an outer surface of the solid electrolyte, a preliminary oxygen concentration control unit configured to control the oxygen concentration inside the preliminary adjustment chamber, a drive control unit configured to control the preliminary oxygen concentration control unit, and a target component acquisition unit configured to acquire concentrations of a first target component and a second target component, on the basis of a difference between a sensor output from the specified component measurement unit at a time of a first operation of the preliminary oxygen concentration control unit, and a sensor output from the specified component measurement unit at a time of a second operation of the preliminary oxygen concentration control unit, and one of the sensor outputs.

The main oxygen concentration control unit includes a main pump cell configured to pump oxygen inside the main oxygen concentration adjustment chamber, by applying a main pump voltage between a main interior side electrode formed in the main oxygen concentration adjustment chamber and an exterior side electrode formed on an outer side of the structural body, and causing a main pump current to flow between the main interior side electrode and the exterior side electrode.

The preliminary oxygen concentration control unit includes a preliminary pump cell configured to pump the oxygen inside the preliminary adjustment chamber, by applying a preliminary pump voltage between an interior side preliminary electrode formed in the preliminary adjustment chamber and the exterior side electrode formed on the outer side of the structural body, and causing a preliminary pump current to flow between the interior side preliminary electrode and the exterior side electrode.

In addition, the main oxygen concentration control unit includes a constant control unit configured to control the preliminary pump voltage of the preliminary pump cell in a manner so that the main pump current of the main pump cell becomes constant.

In accordance with the above-described features, by feeding back the preliminary voltage in order to control the main pump current to remain constant, the preliminary voltage is segregated in accordance with the $O_2$ concentration. As a result, a map can be created indicating a correspondence relationship between the preliminary voltage and the $O_2$ concentration, and using such a map, it becomes possible to accurately detect the NO concentration and the $NH_3$ concentration from the sensor output and the amount of change in the sensor output.

[2] In the first aspect of the gas sensor according to the present invention, the auxiliary oxygen concentration control unit includes an auxiliary pump cell configured to pump the oxygen inside the auxiliary oxygen concentration adjustment chamber, by applying an auxiliary pump voltage between an auxiliary interior side electrode formed in the auxiliary oxygen concentration adjustment chamber and the exterior side electrode formed on the outer side of the structural body, and causing an auxiliary pump current to flow between the auxiliary interior side electrode and the exterior side electrode.

The auxiliary oxygen concentration control unit includes a constant control unit configured to control the main pump voltage of the main pump cell in a manner so that the auxiliary pump current of the auxiliary pump cell becomes constant.

In accordance with these features, a constant control unit feedback-controls the main pump voltage of the main pump cell in a manner so that the auxiliary pump current of the auxiliary pump cell becomes constant.

In this case as well, in the same manner as the gas sensor described above, the NO concentration and the $NH_3$ concentration can be detected with high accuracy from the sensor output and the amount of change in the sensor output.

[3] In a second aspect of a gas sensor according to the present invention, the gas sensor includes a sensor element including a structural body made up from a solid electrolyte that exhibits at least oxygen ion conductivity, a gas introduction port formed in the structural body and into which a gas to be measured is introduced, a main oxygen concentration adjustment chamber communicating with the gas introduction port, an auxiliary oxygen concentration adjustment chamber communicating with the main oxygen concentration adjustment chamber, a measurement chamber communicating with the auxiliary oxygen concentration adjustment chamber, and a preliminary adjustment chamber disposed between the gas introduction port and the main oxygen concentration adjustment chamber, and communicating with the gas introduction port, the gas sensor further including a main oxygen concentration control unit configured to control the oxygen concentration inside the main oxygen concentration adjustment chamber, an auxiliary oxygen concentration control unit configured to control the oxygen concentration inside the auxiliary oxygen concentration adjustment chamber, a temperature control unit configured to control a temperature of the sensor element, a specified component measurement unit configured to measure a concentration of a specified component inside the measurement chamber, electrodes formed on an inner surface and an outer surface of the solid electrolyte, a preliminary oxygen concentration control unit configured to control the oxygen concentration inside the preliminary adjustment chamber, a drive control unit configured to control the preliminary oxygen concentration control unit, and a target component acquisition unit configured to acquire concentrations of a first target component and a second target component, on the basis of a difference between a sensor output from the specified component measurement unit at a time of a first operation of the preliminary oxygen concentration control unit, and a sensor output from the specified component measurement unit at a time of a second operation of the preliminary oxygen concentration control unit, and one of the sensor outputs.

In addition, the main oxygen concentration control unit includes a main pump cell configured to pump the oxygen inside the main oxygen concentration adjustment chamber, by applying a main pump voltage between a main interior side electrode formed in the main oxygen concentration adjustment chamber and an exterior side electrode formed on the outer side of the structural body, and causing a main pump current to flow between the main interior side electrode and the exterior side electrode.

The preliminary oxygen concentration control unit includes a preliminary pump cell configured to pump the oxygen inside the preliminary adjustment chamber, by applying a preliminary pump voltage between an interior side preliminary electrode formed in the preliminary adjustment chamber and the exterior side electrode formed on the outer side of the structural body, and causing a preliminary pump current to flow between the interior side preliminary electrode and the exterior side electrode.

The main oxygen concentration control unit includes a proportional control unit configured to proportionally control the preliminary pump voltage of the preliminary pump cell on the basis of the main pump current of the main pump cell.

In accordance with these features, it is possible to determine the following proportional control equation for proportionally controlling the preliminary pump voltage Vp0 with respect to the preliminary pump current Ip0:

$$Vp0=f(Ip0)=a \cdot Ip0+b$$

On the basis of the proportional control equation, a map can be created indicating a correspondence relationship between the preliminary pump voltage and the $O_2$ concentration, and using such a map, it becomes possible to accurately detect the NO concentration and the $NH_3$ concentration from the sensor output and the amount of change in the sensor output.

[4] In the second aspect of the gas sensor according to the present invention, the preliminary pump voltage preferably is obtained on the basis of $O_2$ concentration, the $O_2$ concentration being determined by the following arithmetic equation:

$$O_2 \text{ concentration}=Ip0+a \times Ip1,$$

wherein a is a constant greater than 1, the preliminary pump current is defined by Ip0, and the main pump current is defined by Ip1.

[5] In the second aspect of the gas sensor according to the present invention, the auxiliary oxygen concentration control unit includes an auxiliary pump cell configured to pump the oxygen inside the auxiliary oxygen concentration adjustment chamber, by applying an auxiliary pump voltage between an auxiliary interior side electrode formed in the auxiliary oxygen concentration adjustment chamber and the exterior side electrode formed on the outer side of the structural body, and causing an auxiliary pump current to flow between the auxiliary interior side electrode and the exterior side electrode. The auxiliary oxygen concentration control unit includes a constant control unit configured to control the main pump voltage of the main pump cell in a manner so that the auxiliary pump current of the auxiliary pump cell becomes constant.

In accordance with these features, since the main pump voltage of the main pump cell is feedback-controlled in a manner so that the auxiliary pump current of the auxiliary pump cell becomes constant, the NO concentration and the $NH_3$ concentration can be accurately detected from the sensor output and the amount of change in the sensor output.

In accordance with the gas sensor according to the present invention, in such a gas sensor, which is capable of accurately measuring over a prolonged period of time the concentration of non-combusted components such as exhaust gas, and a plurality of components (for example, NO, $NH_3$, etc.) that coexist in the presence of oxygen, without being adversely influenced by the capacity of the preliminary adjustment chamber, it is possible to improve the S/N ratio of the sensor output, as well as to make the gas sensor smaller in scale.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 3 is an explanatory diagram schematically showing reactions in a preliminary adjustment chamber, an oxygen concentration adjustment chamber, and a measurement chamber, for a case in which a preliminary pump cell is implementing an OFF operation;

FIG. 4 is an explanatory diagram schematically showing reactions in a preliminary adjustment chamber, an oxygen concentration adjustment chamber, and a measurement chamber, for a case in which the preliminary pump cell is implementing an ON operation;

FIG. 10 is a cross-sectional view in which there is shown one structural example of a second gas sensor according to an embodiment of the present invention;

FIG. 18 is a graph showing results of a fifth exemplary embodiment (a relationship between an $O_2$ concentration and the main pump current Ip1);

DESCRIPTION OF THE PREFERRED EMBODIMENTS

Exemplary embodiments of a gas sensor according to the present invention will be presented and described below with reference to FIGS. 1 to 20. In the present specification, the term "to" when used to indicate a numerical range is used with the implication of including the numerical values written before and after the term as a lower limit value and an upper limit value of the numerical range.

[Configuration of First Gas Sensor]

Figure 1:
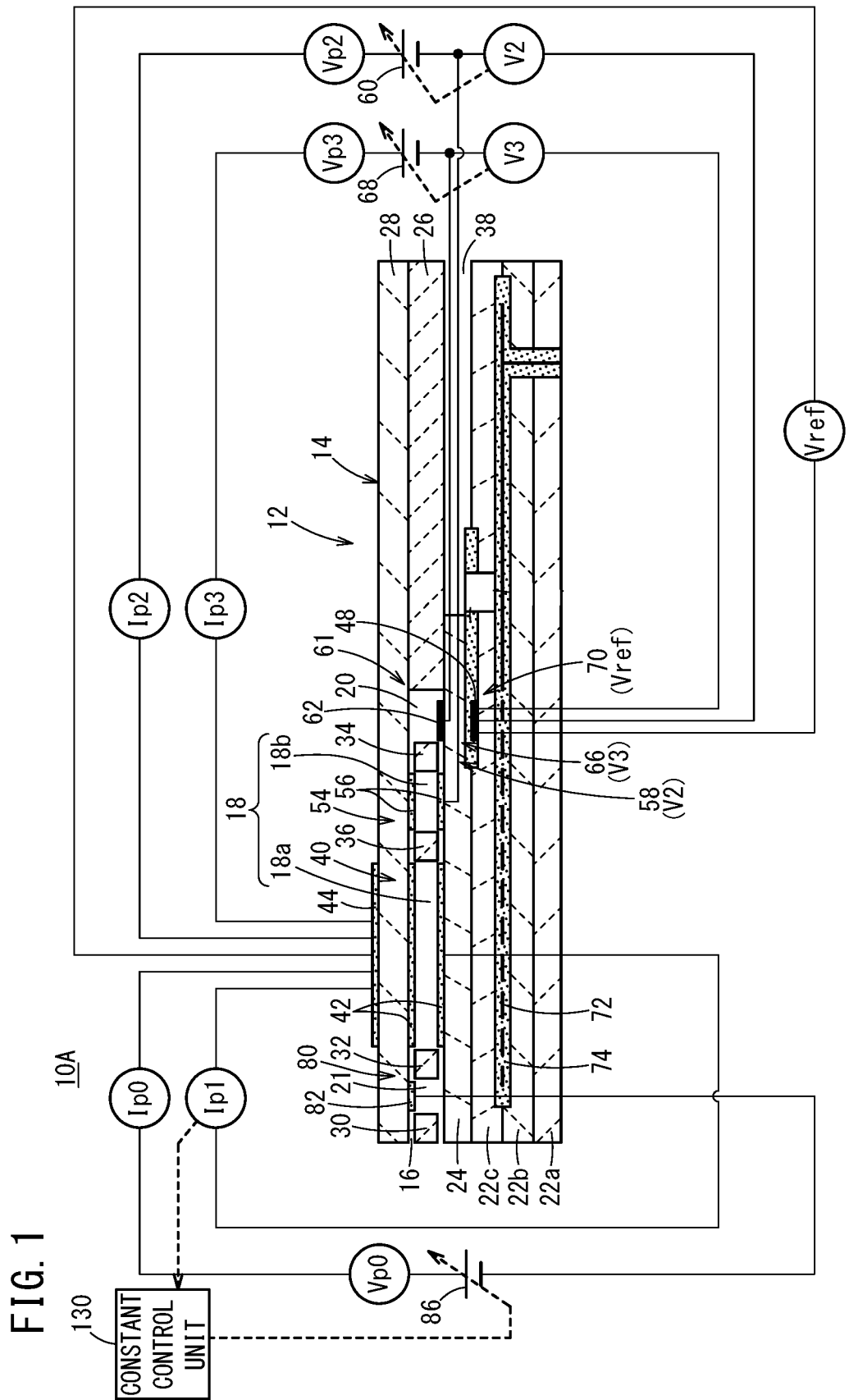
FIG. 1 is a cross-sectional view in which there is shown one structural example of a first gas sensor according to an embodiment of the present invention.
Figure 2:
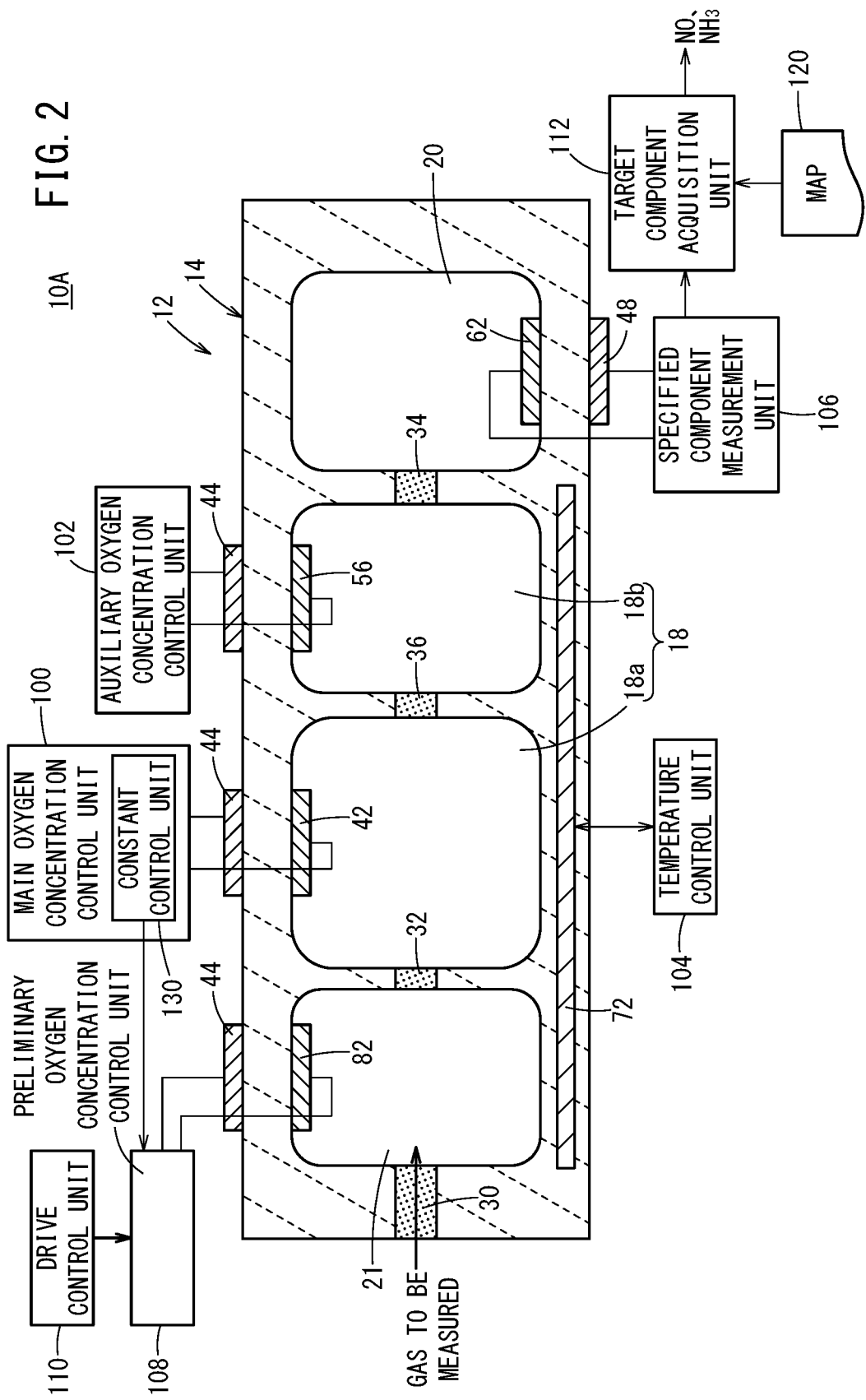
FIG. 2 is a configuration diagram schematically showing a first gas sensor.

As shown in FIGS. 1 and 2, a gas sensor (hereinafter referred to as a first gas sensor 10A) according to a first embodiment includes a sensor element 12. The sensor element 12 includes a structural body 14 made up from a solid electrolyte that exhibits at least oxygen ion conductivity, a gas introduction port 16 formed in the structural body 14 and into which a gas to be measured is introduced, an oxygen concentration adjustment chamber 18 formed in the structural body 14 and communicating with the gas introduction port 16, and a measurement chamber 20 formed in the structural body 14 and communicating with the oxygen concentration adjustment chamber 18.

The oxygen concentration adjustment chamber 18 includes a main adjustment chamber 18a communicating with the gas introduction port 16, and an auxiliary adjustment chamber 18b communicating with the main adjustment chamber 18a. The measurement chamber 20 communicates with the auxiliary adjustment chamber 18b.

Furthermore, the gas sensor 10 includes a preliminary adjustment chamber 21 provided between the gas introduction port 16 and the main adjustment chamber 18a within the structural body 14, and which communicates with the gas introduction port 16.

More specifically, the structural body 14 of the sensor element 12 is constituted by six layers including a first substrate layer 22a, a second substrate layer 22b, a third substrate layer 22c, a first solid electrolyte layer 24, a spacer layer 26, and a second solid electrolyte layer 28, which are stacked in this order from a lower side as viewed in the drawing. The respective layers are composed respectively of an oxygen ion conductive solid electrolyte layer such as zirconia ($ZrO_2$) or the like.

Between a lower surface of the second solid electrolyte layer 28 and an upper surface of the first solid electrolyte layer 24 on a distal end side of the sensor element 12, there are provided the gas introduction port 16, a first diffusion rate control member 30, the preliminary adjustment chamber 21, a second diffusion rate control member 32, the oxygen concentration adjustment chamber 18, a third diffusion rate control member 34, and the measurement chamber 20. Further, a fourth diffusion rate control member 36 is provided between the main adjustment chamber 18a and the auxiliary adjustment chamber 18b that make up the oxygen concentration adjustment chamber 18.

The gas introduction port 16, the first diffusion rate control member 30, the preliminary adjustment chamber 21, the second diffusion rate control member 32, the main adjustment chamber 18a, the fourth diffusion rate control member 36, the auxiliary adjustment chamber 18b, the third diffusion rate control member 34, and the measurement chamber 20 are formed adjacent to each other in a manner communicating in this order. The portion from the gas introduction port 16 leading to the measurement chamber 20 is also referred to as a gas flow section.

The gas introduction port 16, the preliminary adjustment chamber 21, the main adjustment chamber 18a, the auxiliary adjustment chamber 18b, and the measurement chamber 20 are internal spaces provided by hollowing out the spacer layer 26. Any of the preliminary adjustment chamber 21, the main adjustment chamber 18a, the auxiliary adjustment chamber 18b, and the measurement chamber 20 is arranged in a manner so that respective upper parts thereof are defined by a lower surface of the second solid electrolyte layer 28, respective lower parts thereof are defined by an upper surface of the first solid electrolyte layer 24, and respective side parts thereof are defined by side surfaces of the spacer layer 26.

Any of the first diffusion rate control member 30, the third diffusion rate control member 34, and the fourth diffusion rate control member 36 is provided as two horizontally elongated slits (in which openings thereof have a longitudinal direction in a direction perpendicular to the drawing). The second diffusion rate control member 32 is provided as one horizontally elongated slit (in which an opening thereof has a longitudinal direction in a direction perpendicular to the drawing).

Further, a reference gas introduction space 38 is disposed between an upper surface of the third substrate layer 22c and a lower surface of the spacer layer 26, at a position that is farther from the distal end side than the gas flow section. The reference gas introduction space 38 is an internal space in which an upper part thereof is defined by a lower surface of the spacer layer 26, a lower part thereof is defined by an upper surface of the third substrate layer 22c, and a side part thereof is defined by a side surface of the first solid electrolyte layer 24. For example, oxygen or atmospheric air is introduced as a reference gas into the reference gas introduction space 38.

The gas introduction port 16 is a location that opens with respect to the external space, and the target gas to be measured is drawn into the sensor element 12 from the external space through the gas introduction port 16.

The first diffusion rate control member 30 is a location that imparts a predetermined diffusion resistance to the gas to be measured which is introduced from the gas introduction port 16 into the preliminary adjustment chamber 21. The second diffusion rate control member 32 is a location that imparts a predetermined diffusion resistance to the gas to be measured which is introduced from the preliminary adjustment chamber 21 into the main adjustment chamber 18a.

The main adjustment chamber 18a is provided as a space for the purpose of adjusting an oxygen partial pressure within the gas to be measured that is introduced from the gas introduction port 16. The oxygen partial pressure is adjusted by operation of a main pump cell 40.

The main pump cell 40 comprises an electrochemical pump cell, which is constituted by a main interior side pump electrode 42, an exterior side pump electrode 44, and an oxygen ion conductive solid electrolyte which is sandwiched between the two pump electrodes. The main interior side pump electrode 42 is provided substantially over the entire surface of an upper surface of the first solid electrolyte layer 24, a lower surface of the second solid electrolyte layer 28, and side surfaces of the spacer layer 26 that define the main adjustment chamber 18a. The exterior side pump electrode 44 is provided in a condition of being exposed to the external space in a region corresponding to the main interior side pump electrode 42 on the upper surface of the second solid electrolyte layer 28. The main interior side pump electrode 42 is made of a material that weakens the reduction capability with respect to the NOx component within the gas to be measured. For example, the pump electrodes are formed as porous cermet electrodes (for example, cermet electrodes of $ZrO_2$ and a noble metal such as Pt containing 0.1 to 30.0 wt % of Au) having rectangular shapes as viewed in plan.

The main pump cell 40 pumps oxygen in the interior of the main adjustment chamber 18a out into the external space, or alternatively, pumps oxygen in the external space into the main adjustment chamber 18a, thereby enabling the main pump current Ip1 to flow between the exterior side pump electrode 44 and the main interior side pump electrode 42.

The fourth diffusion rate control member 36 imparts a predetermined diffusion resistance to the gas to be measured, the oxygen concentration (oxygen partial pressure) of which is controlled by operation of the main pump cell 40 in the main adjustment chamber 18a, and is a location that guides the gas to be measured into the auxiliary adjustment chamber 18b.

The auxiliary adjustment chamber 18b is provided as a space for further carrying out adjustment of the oxygen partial pressure by an auxiliary pump cell 54, with respect to the gas to be measured which is introduced through the fourth diffusion rate control member 36, after the oxygen concentration (oxygen partial pressure) has been adjusted beforehand in the main adjustment chamber 18a. In accordance with this feature, the oxygen concentration inside the auxiliary adjustment chamber 18b can be kept constant with high accuracy, and therefore, the gas sensor 10 is made capable of measuring the NOx concentration with high accuracy.

The auxiliary pump cell 54 is an electrochemical pump cell, and is constituted by an auxiliary pump electrode 56, which is provided substantially over the entirety of the lower surface of the second solid electrolyte layer 28 facing toward the auxiliary adjustment chamber 18b, the exterior side pump electrode 44, and the second solid electrolyte layer 28.

Moreover, in the same manner as the main interior side pump electrode 42, the auxiliary pump electrode 56 is also formed using a material that weakens the reduction capability with respect to the NOx component within the gas to be measured.

The auxiliary pump cell 54, by applying a desired second pump voltage Vp2 (auxiliary pump voltage) between the auxiliary pump electrode 56 and the exterior side pump electrode 44, is capable of pumping out oxygen within the atmosphere inside the auxiliary adjustment chamber 18b into the external space, or alternatively, is capable of pumping in oxygen from the external space into the auxiliary adjustment chamber 18b.

Further, in order to control the oxygen partial pressure within the atmosphere inside the auxiliary adjustment chamber 18b, an electrochemical sensor cell, and more specifically, an auxiliary oxygen partial pressure detecting sensor cell 58 for controlling the auxiliary pump, is constituted by the auxiliary pump electrode 56, a reference electrode 48, the second solid electrolyte layer 28, the spacer layer 26, and the first solid electrolyte layer 24.

Moreover, the auxiliary pump cell 54 carries out pumping by a first variable power source 60, the voltage of which is controlled based on a second electromotive force V2 detected by the auxiliary oxygen partial pressure detecting sensor cell 58. Consequently, the oxygen partial pressure within the atmosphere inside the auxiliary adjustment chamber 18b is controlled so as to become a low partial pressure that does not substantially influence the measurement of NOx.

Further, together therewith, an auxiliary pump current Ip2 of the auxiliary pump cell 54 is used so as to control the second electromotive force V2 of the auxiliary oxygen partial pressure detecting sensor cell 58. More specifically, the auxiliary pump current Ip2 is input as a control signal to the auxiliary oxygen partial pressure detecting sensor cell 58, and by controlling the second electromotive force V2, the gradient of the oxygen partial pressure within the gas to be measured, which is introduced through the fourth diffusion rate control member 36 into the auxiliary adjustment chamber 18b, is controlled so as to remain constant at all times. When the first gas sensor 10A is used as a NOx sensor, by the actions of the main pump cell 40 and the auxiliary pump cell 54, the oxygen concentration inside the auxiliary adjustment chamber 18b is maintained at a predetermined value with high accuracy for each of the respective conditions.

The third diffusion rate control member 34 imparts a predetermined diffusion resistance to the gas to be measured, the oxygen concentration (oxygen partial pressure) of which is controlled by operation of the auxiliary pump cell 54 in the auxiliary adjustment chamber 18b, and is a location that guides the gas to be measured into the measurement chamber 20.

Measurement of the NOx concentration is primarily performed by operations of a measurement pump cell 61 provided in the measurement chamber 20. The measurement pump cell 61 is an electrochemical pump cell constituted by a measurement electrode 62, the exterior side pump electrode 44, the second solid electrolyte layer 28, the spacer layer 26, and the first solid electrolyte layer 24. The measurement electrode 62 is provided, for example, directly on the upper surface of the first solid electrolyte layer 24 inside the measurement chamber 20, and is a porous cermet electrode made of a material whose reduction capability with respect to the NOx component within the gas to be measured is higher than that of the main interior side pump electrode 42. The measurement electrode 62 also functions as a NOx reduction catalyst for reducing NOx existing within the atmosphere above the measurement electrode 62.

The measurement pump cell 61 is capable of pumping out oxygen that is generated by decomposition of nitrogen oxide within the atmosphere around the periphery of the measurement electrode 62 (inside the measurement chamber 20), and can detect the generated amount as a measured pump current Ip3, or stated otherwise, as the sensor output.

Further, in order to detect the oxygen partial pressure around the periphery of the measurement electrode 62 (inside the measurement chamber 20), an electrochemical sensor cell, and more specifically, a third oxygen partial pressure detecting sensor cell 66 for controlling the measurement pump, is constituted by the first solid electrolyte layer 24, the measurement electrode 62, and the reference electrode 48. A second variable power source 68 is controlled based on a third electromotive force V3 detected by the third oxygen partial pressure detecting sensor cell 66.

The gas to be measured, which is introduced into the auxiliary adjustment chamber 18b, reaches the measurement electrode 62 inside the measurement chamber 20 through the third diffusion rate control member 34, under a condition in which the oxygen partial pressure is controlled. Nitrogen oxide existing within the gas to be measured around the periphery of the measurement electrode 62 is reduced to thereby generate oxygen. Then, the generated oxygen is subjected to pumping by the measurement pump cell 61. At this time, a third pump voltage Vp3 of the second variable power source 68 is controlled in a manner so that the third electromotive force V3 detected by the third oxygen partial pressure detecting sensor cell 66 becomes constant. The amount of oxygen generated around the periphery of the measurement electrode 62 is proportional to the concentration of nitrogen oxide within the gas to be measured. Accordingly, the nitrogen oxide concentration within the gas to be measured can be calculated using the measured pump current Ip3 of the measurement pump cell 61. More specifically, the measurement pump cell 61 constitutes a specified component measurement unit 106 that measures the concentration of a specified component (NO) in the measurement chamber 20.

Further, the first gas sensor 10A includes an electrochemical sensor cell 70. The sensor cell 70 includes the second solid electrolyte layer 28, the spacer layer 26, the first solid electrolyte layer 24, the third substrate layer 22c, the exterior side pump electrode 44, and the reference electrode 48. In accordance with the electromotive force Vref obtained by the sensor cell 70, it is possible to detect the oxygen partial pressure within the gas to be measured existing externally of the sensor.

Furthermore, in the sensor element 12, a heater 72 is formed in a manner of being sandwiched from above and below between the second substrate layer 22b and the third substrate layer 22c. The heater 72 generates heat by being supplied with power from the exterior through a non-illustrated heater electrode provided on a lower surface of the first substrate layer 22a. As a result of the heat generated by the heater 72, the oxygen ion conductivity of the solid electrolyte that constitutes the sensor element 12 is enhanced. The heater 72 is embedded over the entire region of the preliminary adjustment chamber 21 and the oxygen concentration adjustment chamber 18, and a predetermined location of the sensor element 12 can be heated and maintained at a predetermined temperature. Moreover, a heater insulating layer 74 made of alumina or the like is formed on upper and lower surfaces of the heater 72, for the purpose of obtaining electrical insulation thereof from the second substrate layer 22b and the third substrate layer 22c (hereinafter, the heater 72, the heater electrode, and the heater insulating layer 74 may also be referred to collectively as a heater portion).

In addition, the preliminary adjustment chamber 21 is driven by a later-described drive control unit 110 (see FIG. 2), and during driving thereof, functions as a space for adjusting the oxygen partial pressure within the gas to be measured which is introduced from the gas introduction port 16. The oxygen partial pressure is adjusted by operation of a preliminary pump cell 80.

The preliminary pump cell 80 is a preliminary electrochemical pump cell, and is constituted by a preliminary pump electrode 82, which is provided substantially over the entirety of the lower surface of the second solid electrolyte layer 28 facing toward the preliminary adjustment chamber 21, the exterior side pump electrode 44, and the second solid electrolyte layer 28.

Moreover, in the same manner as the main interior side pump electrode 42, the preliminary pump electrode 82 is also formed using a material that weakens the reduction capability with respect to the NOx component within the gas to be measured.

The preliminary pump cell 80, by applying a desired preliminary pump voltage Vp0 by the third variable power source 86 between the preliminary pump electrode 82 and the exterior side pump electrode 44, is capable of pumping out oxygen within the atmosphere inside the preliminary adjustment chamber 21 into the external space, or alternatively, is capable of pumping in oxygen from the external space into the preliminary adjustment chamber 21.

The preliminary adjustment chamber 21 also functions as a buffer space. More specifically, it is possible to cancel fluctuations in the concentration of the gas to be measured, which are caused by pressure fluctuations of the gas to be measured in the external space (pulsations in the exhaust pressure, in the case that the gas to be measured is an exhaust gas of an automobile).

Furthermore, as shown schematically in FIG. 2, the first gas sensor 10A includes a main oxygen concentration control unit 100 that controls the oxygen concentration inside the main adjustment chamber 18a, an auxiliary oxygen concentration control unit 102 that controls the oxygen concentration inside the auxiliary adjustment chamber 18b, a temperature control unit 104 that controls the temperature of the sensor element 12, a specified component measurement unit 106 that measures the concentration of a specified component (NO) inside the measurement chamber 20, a preliminary oxygen concentration control unit 108, a drive control unit 110, and a target component acquisition unit 112.

Moreover, these various units are each constituted by one or more electronic circuits having, for example, one or a plurality of CPUs (central processing units), memory devices, and the like. The electronic circuits are software-based functional units in which predetermined functions are realized, for example, by the CPUs executing programs stored in a storage device. Of course, the electronic circuits may be constituted by an integrated circuit such as an FPGA (Field-Programmable Gate Array), in which the plurality of electronic circuits are connected according to the functions thereof.

In the conventional technique, after having carried out conversion into NO with respect to all of the target components of NO and $NH_3$ existing inside the oxygen concentration adjustment chamber 18, the target components are introduced into the measurement chamber 20, and a total amount of the two components is measured. Stated otherwise, it has been impossible to measure the concentrations of each of the two target components, that is, the respective concentrations of NO and $NH_3$.

In contrast thereto, by being equipped with the various units discussed above, the gas sensor 10 is configured to be capable of acquiring the respective concentrations of NO and $NH_3$.

More specifically, the main oxygen concentration control unit 100 controls the preliminary oxygen concentration control unit 108 on the basis of the main pump current Ip1 of the main pump cell 40. The preliminary oxygen concentration control unit 108 adjusts the oxygen concentration in the preliminary adjustment chamber 21 to a concentration in accordance with predetermined conditions, through control performed by the main oxygen concentration control unit 100.

On the basis of the preset oxygen concentration condition, and the second electromotive force V2 generated in the auxiliary oxygen partial pressure detecting sensor cell 58

(see FIG. 1), the auxiliary oxygen concentration control unit 102 feedback-controls the first variable power source 60, thereby adjusting the oxygen concentration inside the auxiliary adjustment chamber 18b to a concentration in accordance with the above-described condition.

The temperature control unit 104 feedback-controls the heater 72 on the basis of a preset sensor temperature condition, and the measured value from a temperature sensor (not shown) that measures the temperature of the sensor element 12, whereby the temperature of the sensor element 12 is adjusted to a temperature in accordance with the above-described condition.

The specified component measurement unit 106 measures the concentration of the specified component (NO component) inside the measurement chamber 20. In particular, the NO component at the time of an ON operation of the preliminary oxygen concentration control unit 108, and the NO component at the time of an OFF operation of the preliminary oxygen concentration control unit 108 are measured.

The target component acquisition unit 112 acquires the respective concentrations of NO and $NH_3$ on the basis of a difference between the sensor output from the specified component measurement unit 106 in accordance with a first operation (for example, the ON operation) of the preliminary oxygen concentration control unit 108, and the sensor output from the specified component measurement unit 106 in accordance with a second operation (for example, the OFF operation) of the preliminary oxygen concentration control unit 108.

By the main oxygen concentration control unit 100, the auxiliary oxygen concentration control unit 102, or the temperature control unit 104, or alternatively, by the main oxygen concentration control unit 100, the auxiliary oxygen concentration control unit 102, and the temperature control unit 104, the first gas sensor 10A performs a control so as to convert all of the $NH_3$ into NO, without causing decomposition of NO inside the oxygen concentration adjustment chamber 18.

In addition, the target component acquisition unit 112 acquires the respective concentrations of NO and $NH_3$ on the basis of a difference between the sensor output from the specified component measurement unit 106 in accordance with the ON operation of the preliminary oxygen concentration control unit 108, and the sensor output from the specified component measurement unit 106 in accordance with the OFF operation of the preliminary oxygen concentration control unit 108.

Next, processing operations of the first gas sensor 10A will be described with reference also to FIGS. 3 and 4.

First, as shown in FIG. 3, the $NH_3$ that was introduced through the gas introduction port 16 reaches the oxygen concentration adjustment chamber 18 during a period in which the preliminary oxygen concentration control unit 108 is implementing the OFF operation by the drive control unit 110. In the oxygen concentration adjustment chamber 18, by operation of the main oxygen concentration control unit 100, a control is performed so as to convert all of the $NH_3$ into NO, and therefore, the $NH_3$ that has flowed into the oxygen concentration adjustment chamber 18 from the preliminary adjustment chamber 21 causes an oxidation reaction of $NH_3 \rightarrow NO$ to occur inside the oxygen concentration adjustment chamber 18, and all of the $NH_3$ inside the oxygen concentration adjustment chamber 18 is converted into NO. Accordingly, the $NH_3$ that was introduced through the gas introduction port 16 passes through the first diffusion rate control member 30 and the second diffusion rate control member 32 at a speed of the $NH_3$ diffusion coefficient of 2.2 $cm^2/sec$, and after being converted into NO inside the oxygen concentration adjustment chamber 18, passes through the third diffusion rate control member 34 at a speed of the NO diffusion coefficient of 1.8 $cm^2/sec$, and moves into the adjacent measurement chamber 20.

On the other hand, during a period in which the preliminary oxygen concentration control unit 108 is implementing the ON operation by the drive control unit 110, as shown in FIG. 4, the oxidation reaction of $NH_3 \rightarrow NO$ occurs inside the preliminary adjustment chamber 21, and all of the $NH_3$ that was introduced through the gas introduction port 16 is converted into NO. Accordingly, the $NH_3$ passes through the first diffusion rate control member 30 at an $NH_3$ diffusion coefficient of 2.2 $cm^2/sec$, and thereafter the converted NO passes through the second diffusion rate control member 32 and the third diffusion rate control member 34, which lie beyond the preliminary adjustment chamber 21, at a speed of the NO diffusion coefficient of 1.8 $cm^2/sec$, and moves into the measurement chamber 20.

Stated otherwise, by switching the preliminary oxygen concentration control unit 108 from the second operative state to the first operative state, the location where the oxidation reaction of $NH_3$ takes place is moved from the oxygen concentration adjustment chamber 18 to the preliminary adjustment chamber 21.

Changing of the location where the oxidation reaction of $NH_3$ takes place, from the oxygen concentration adjustment chamber 18 to the preliminary adjustment chamber 21 is equivalent to changing of a state of the $NH_3$ in the target gas when passing through the second diffusion rate control member 32, from $NH_3$ to NO. In addition, since NO and $NH_3$ possess different diffusion coefficients, the difference between passing through the second diffusion rate control member 32 with NO or passing therethrough with $NH_3$ corresponds to a difference in the amount of NO that flows into the measurement chamber 20, and therefore, the measured pump current Ip3 that flows to the measurement pump cell 61 is made to change.

In this case, the measurement pump current Ip3(on) when the preliminary pump cell 80 is implementing the ON operation, and the amount of change ΔIp3 in the measurement pump current Ip3(off) when the preliminary pump cell 80 is implementing the OFF operation are uniquely determined by the concentration of $NH_3$ in the gas to be measured. Therefore, it is possible to calculate the respective concentrations of NO and $NH_3$ from the measurement pump current Ip3(on) or Ip3(off) at the time that the preliminary pump cell 80 is ON or OFF, and the amount of change ΔIp3 in the aforementioned measurement pump current Ip3.

Accordingly, with the target component acquisition unit 112, the respective concentrations of NO and $NH_3$ are acquired on the basis of the measured pump current Ip3(1) at the time of the ON operation of the preliminary pump cell 80, the amount of change ΔIp3 between the measured pump current Ip3(1) and the measured pump current Ip3(2) at the time of the OFF operation of the preliminary pump cell 80, and the map 120.

In addition, the main oxygen concentration control unit 100 of the first gas sensor 10A includes a constant control unit 130 that controls the preliminary pump voltage Vp0 of the preliminary pump cell 80 in a manner so that the main pump current Ip1 of the main pump cell 40 becomes constant.

In accordance with this feature, by feeding back the preliminary pump voltage Vp0 in order to control the main pump current Ip1 to remain constant, the preliminary pump voltage Vp0 becomes segregated in accordance with the $O_2$ concentration. As a result, since the position of the points differ depending on the differences of the $O_2$ concentration, the NO concentration, and the $NH_3$ concentration, by mapping these relationships and creating the map 120, it becomes possible to accurately detect the NO concentration and the $NH_3$ concentration from the sensor output Ip3 and the amount of change ΔIp3 in the sensor output.

First Exemplary Embodiment

A first exemplary embodiment will now be described with reference to FIGS. 5A and 5B. In the first exemplary embodiment, in the first gas sensor 10A shown in FIG. 1, a relationship between the main pump current Ip1 at each of oxygen partial pressures and the preliminary pump voltage Vp0, and more specifically, a change in the preliminary pump voltage Vp0 depending on the $O_2$ concentration, was confirmed.

The conditions for implementing the first exemplary embodiment were as follows.
  Sensor Drive Temperature: 840° C.
  Model Gases: $O_2$ and $H_2O$ (without introduction of NO and $NH_3$)
  Gas Concentration: $O_2$=1 to 20%, $H_2O$=3%
  Gas Flow Rate: 200 L/min (at 250° C.)

Figures 5A, 5B:
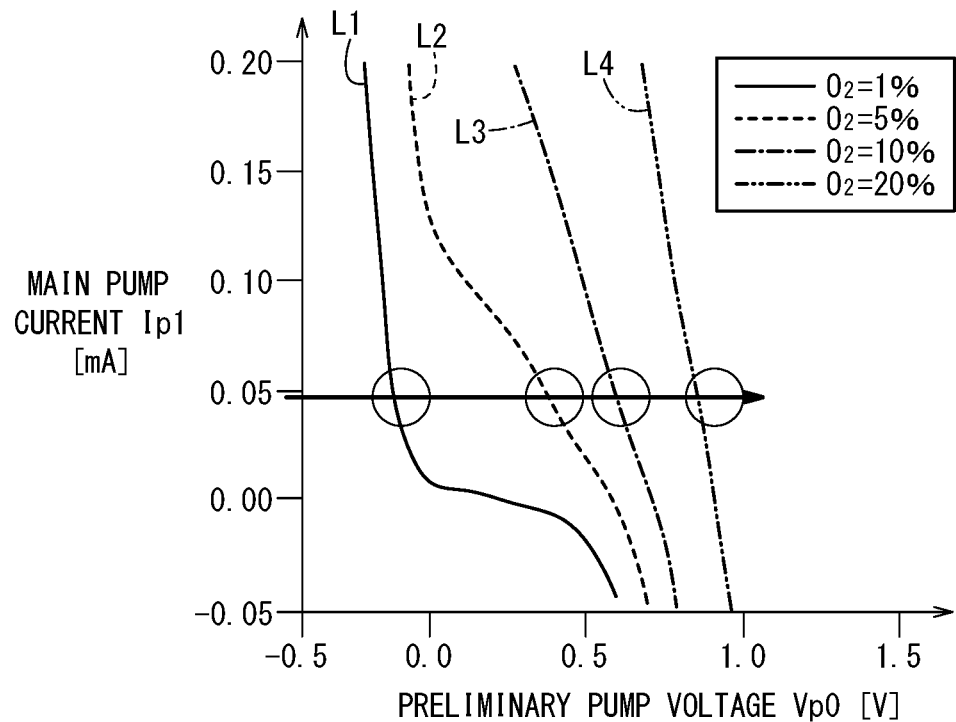
FIG. 5A is a graph showing results of a first exemplary embodiment (a relationship between a preliminary pump voltage Vp0 and a main pump current Ip1)
FIG. 5B is a table indicating results of the first exemplary embodiment (a relationship between an $O_2$ concentration and the preliminary pump voltage Vp0)

The measurement results are shown in the graph of FIG. 5A and the table of FIG. 5B. In the graph of FIG. 5A, a characteristic when the $O_2$ concentration is 1% is shown by the curve L1, a characteristic when the $O_2$ concentration is 5% is shown by the curve L2, a characteristic when the $O_2$ concentration is 10% is shown by the curve L3, and a characteristic when the $O_2$ concentration is 20% is shown by the curve L4.

The table of FIG. 5B shows the preliminary pump voltage Vp0 when the $O_2$ concentration is 1%, 5%, 10%, and 20%, and the main pump current Ip1 is 0.05 mA.

In the foregoing manner, by feeding back the preliminary pump voltage Vp0 in order to control the main pump current Ip1 to remain constant, it was understood that the preliminary pump voltage Vp0 is segregated in accordance with the $O_2$ concentration.

Second Exemplary Embodiment

The second exemplary embodiment differs from the first exemplary embodiment in that NO and $NH_3$ are added as model gases in addition to $O_2$ and $H_2O$.

The conditions for implementing the second exemplary embodiment were as follows.
  Sensor Drive Temperature: 840° C.
  Model Gases: $O_2$, $H_2O$, NO, $NH_3$
  Gas Concentration: $O_2$=1 to 20%, $H_2O$=3%, NO=0 to 500 ppm, $NH_3$=0 to 500 ppm
  Gas Flow Rate: 200 L/min (at 250° C.)

Changes in the sensor output Ip3 in accordance with the NO concentration and the $NH_3$ concentration in a state in which driving of the preliminary pump cell 80 was turned OFF, and trends in the amount of change ΔIp3 in the sensor output Ip3 due to the $NH_3$ concentration were confirmed by changing the NO concentration and the $NH_3$ concentration. The results thereof are shown in FIGS. 6A to 7B.

Figure 6A:
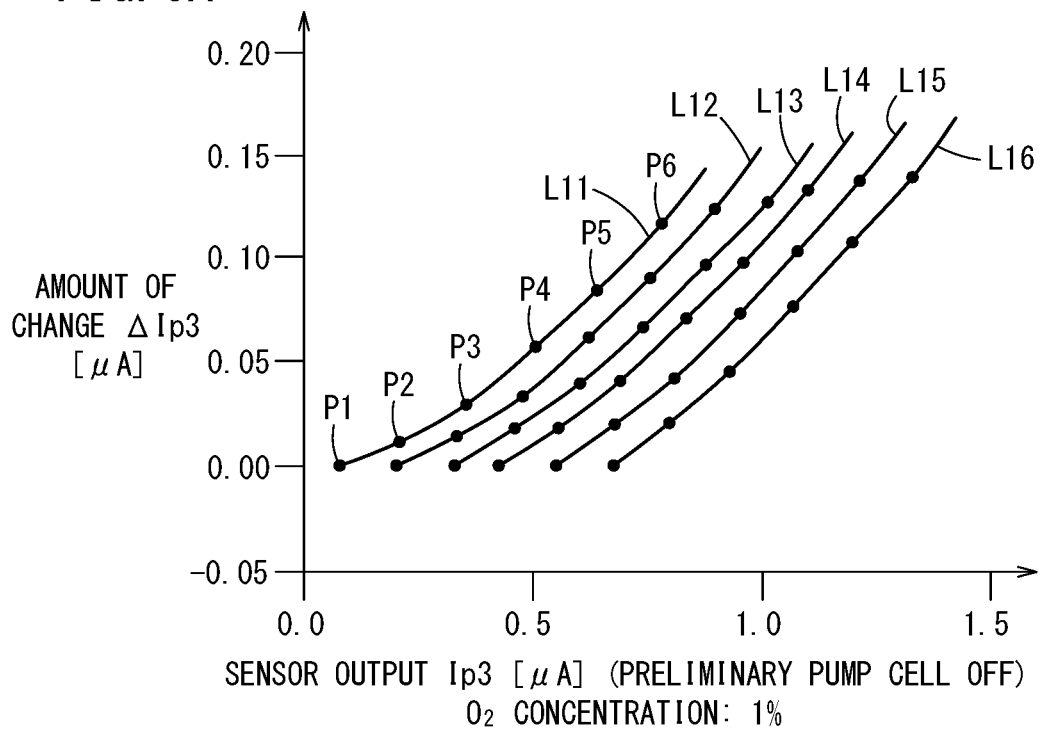
FIG. 6A is a graph showing results of a second exemplary embodiment (a relationship between a sensor output Ip3 and an amount of change $\Delta Ip3$ in the sensor output at an $O_2$ concentration of 1%)
Figure 6B:
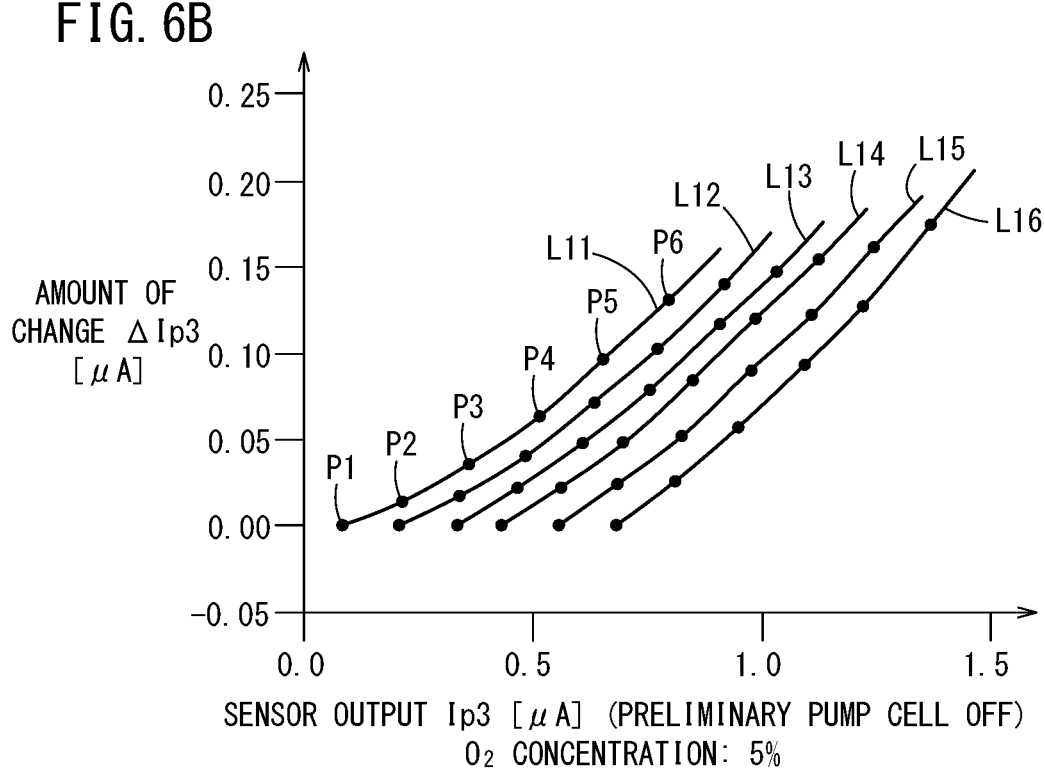
FIG. 6B is a graph showing results of the second exemplary embodiment (a relationship between the sensor output Ip3 and the amount of change $\Delta Ip3$ in the sensor output at an $O_2$ concentration of 5%)
Figure 7A:
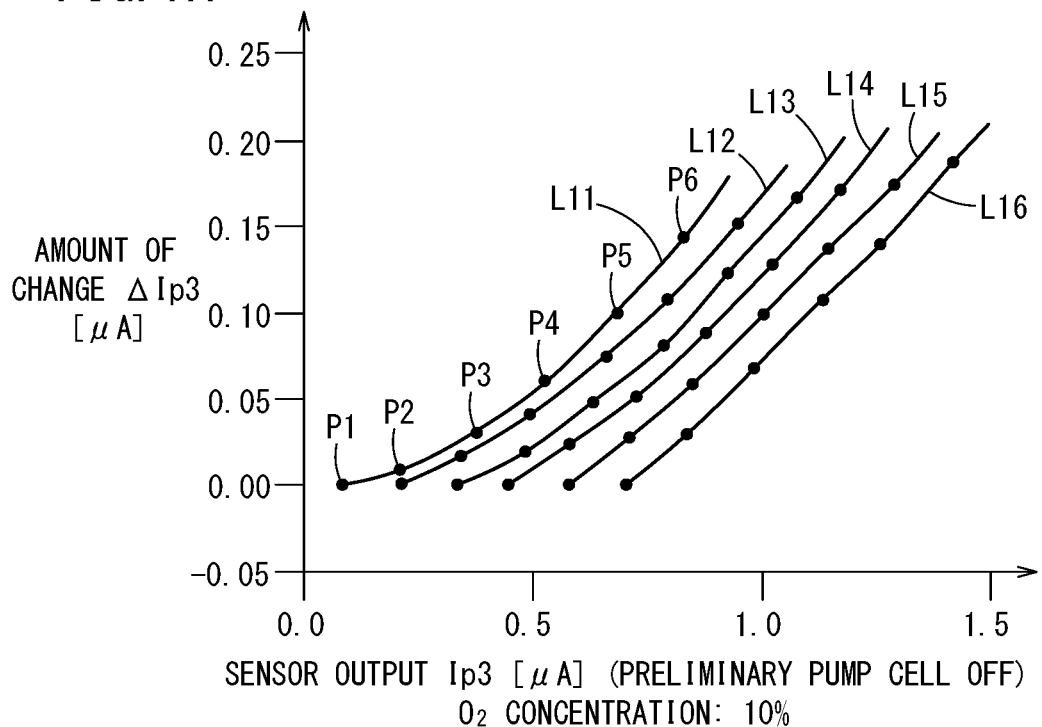
FIG. 7A is a graph showing results of the second exemplary embodiment (a relationship between the sensor output Ip3 and the amount of change $\Delta Ip3$ in the sensor output at an $O_2$ concentration of 10%)
Figure 7B:
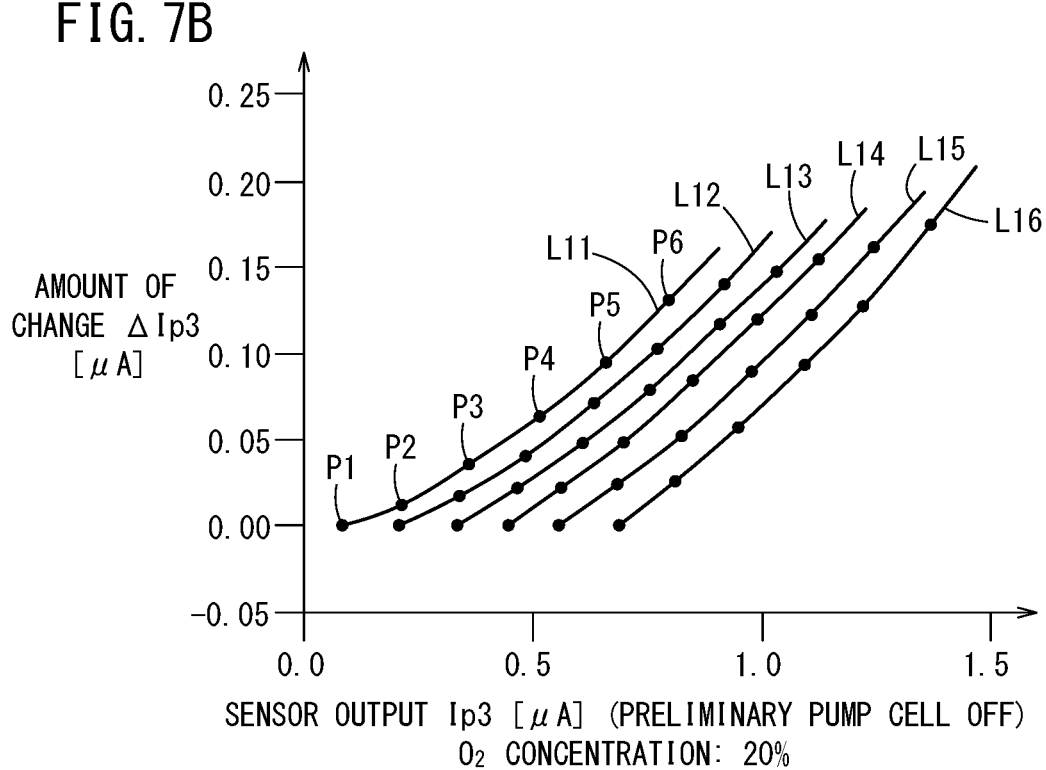
FIG. 7B is a graph showing results of the second exemplary embodiment (a relationship between the sensor output Ip3 and the amount of change $\Delta Ip3$ in the sensor output at an $O_2$ concentration of 20%)
Figure 8A:
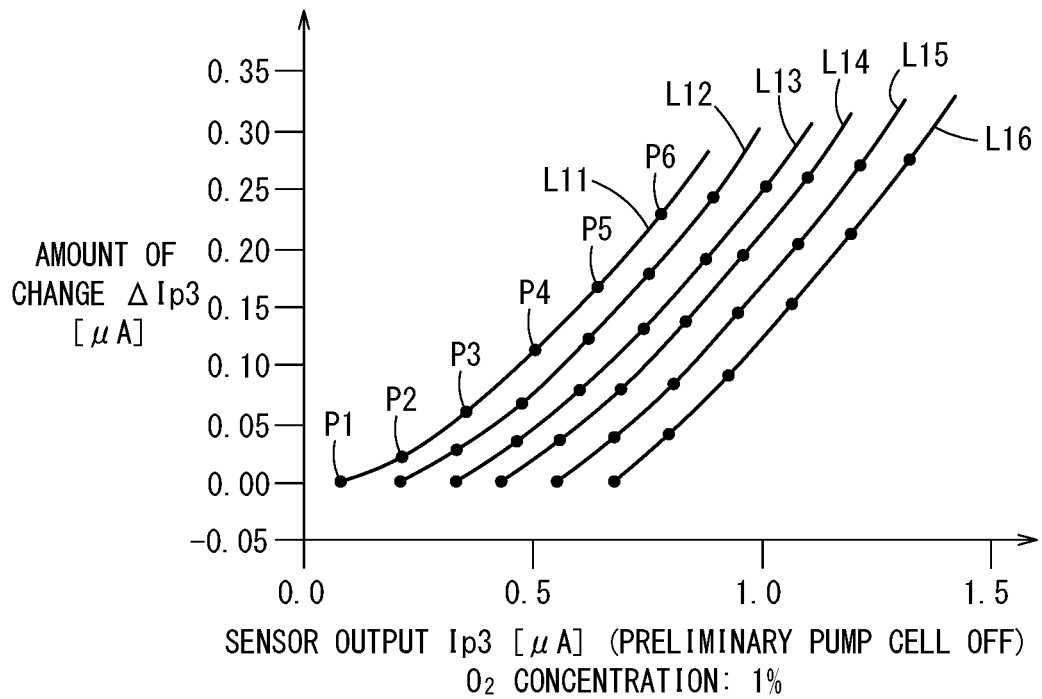
FIG. 8A is a graph showing results of a first comparative example (a relationship between a sensor output Ip3 and an amount of change $\Delta Ip3$ in the sensor output at an $O_2$ concentration of 1%)
Figure 8B:
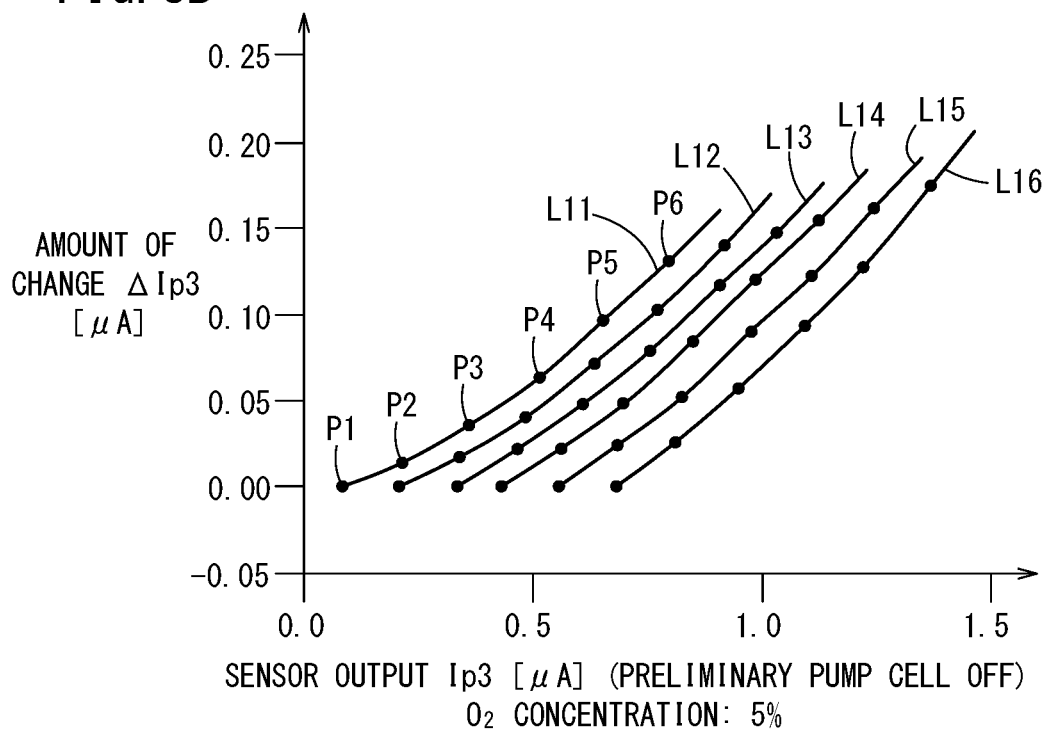
FIG. 8B is a graph showing results of the first comparative example (a relationship between the sensor output Ip3 and the amount of change $\Delta Ip3$ in the sensor output at an $O_2$ concentration of 5%)

FIG. 6A shows characteristics when the $O_2$ concentration is 1%, and FIG. 6B shows characteristics when the $O_2$ concentration is 5%. Further, FIG. 7A shows characteristics when the $O_2$ concentration is 10%, and FIG. 7B shows characteristics when the $O_2$ concentration is 20%.

In FIGS. 6A to 7B, a characteristic when the NO concentration is 0 ppm is shown by the curve L11, a characteristic when the NO concentration is 100 ppm is shown by the curve L12, a characteristic when the NO concentration is 200 ppm is shown by the curve L13, a characteristic when the NO concentration is 300 ppm is shown by the curve L14, a characteristic when the NO concentration is 400 ppm is shown by the curve L15, and a characteristic when the NO concentration is 500 ppm is shown by the curve L16.

Further, in FIGS. 6A to 7B, a point when the $NH_3$ concentration is 0 ppm is indicated by P1, a point when the $NH_3$ concentration is 100 ppm is indicated by P2, a point when the $NH_3$ concentration is 200 ppm is indicated by P3, a point when the $NH_3$ concentration is 300 ppm is indicated by P4, a point when the $NH_3$ concentration is 400 ppm is indicated by P5, and a point when the $NH_3$ concentration is 500 ppm is indicated by P6.

As can be understood from FIGS. 6A to 7B, since the positions of the points differ depending on the differences of the $O_2$ concentration, the NO concentration, and the $NH_3$ concentration, by mapping the relationships shown in FIGS. 6A to 7B and creating the map 120, it becomes possible to accurately detect the NO concentration and the $NH_3$ concentration from the sensor output Ip3 and the amount of change ΔIp3 in the sensor output.

First Comparative Example

In the first comparative example, a gas sensor is used having substantially the same configuration as that of the aforementioned second exemplary embodiment, but differs therefrom in that the preliminary pump voltage Vp0 is controlled so as to be kept at a constant voltage (=0.35 V).

In the measurement method, similar to the second exemplary embodiment, changes in the sensor output Ip3 in accordance with the NO concentration and the $NH_3$ concentration in a state in which driving of the preliminary pump cell 80 was turned OFF, and trends in the amount of change ΔIp3 in the sensor output Ip3 due to the $NH_3$ concentration were confirmed by changing the NO concentration and the $NH_3$ concentration. The results thereof are shown in FIGS. 8A to 9B.

Figure 9A:
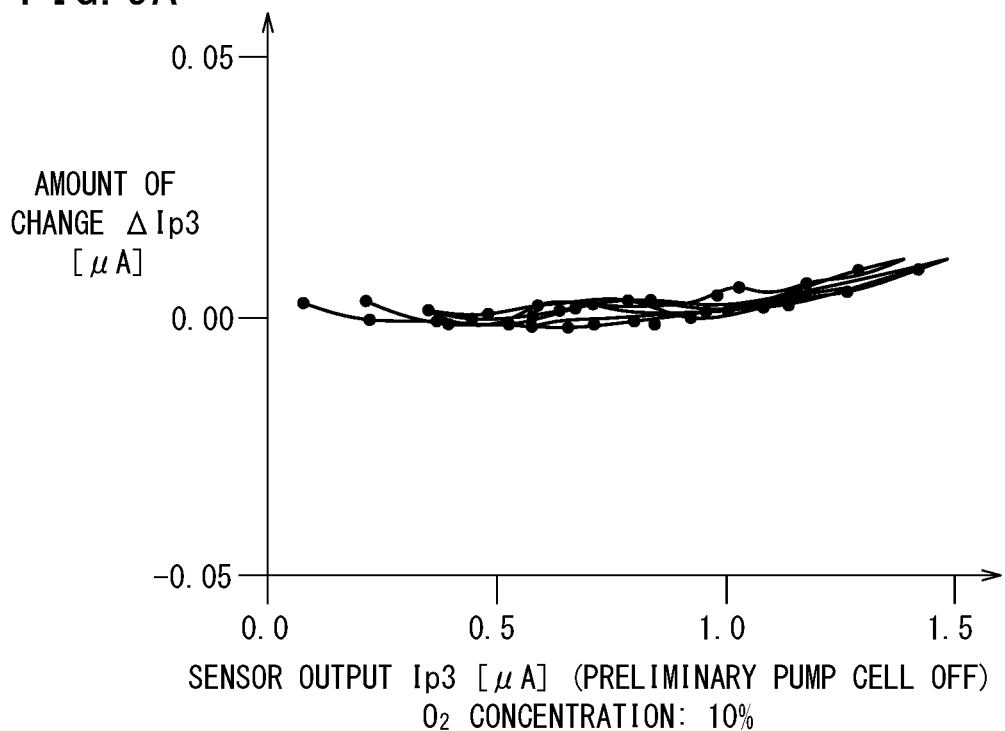
FIG. 9A is a graph showing results of the first comparative example (a relationship between a sensor output Ip3 and an amount of change $\Delta Ip3$ in the sensor output at an $O_2$ concentration of 10%)
Figure 9B:
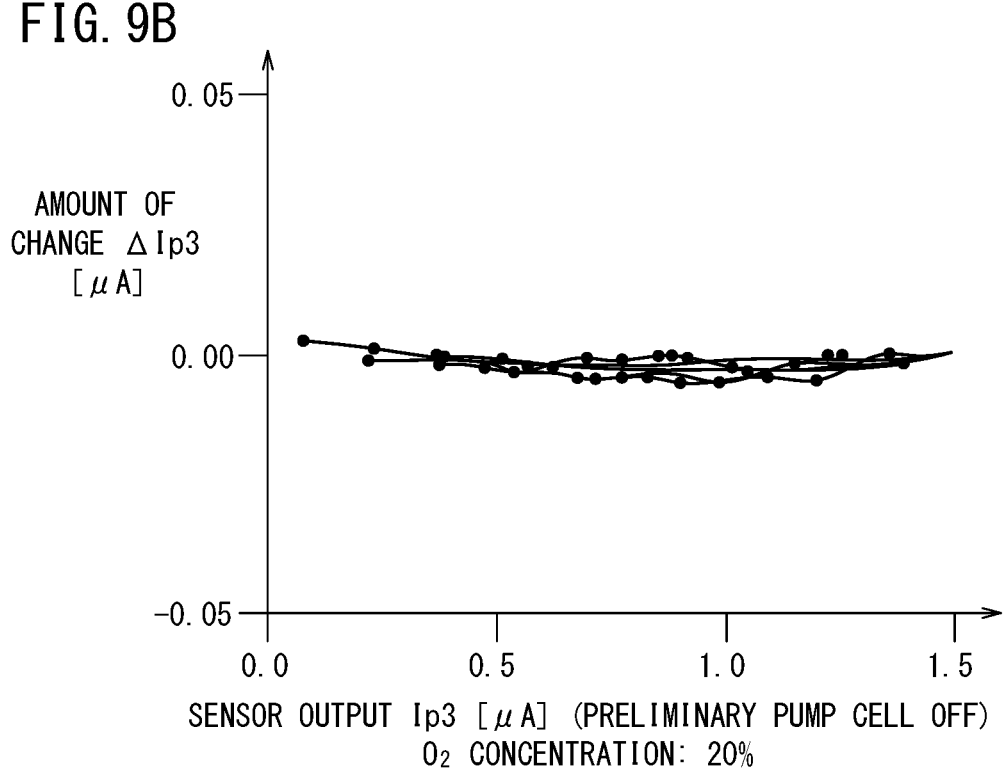
FIG. 9B is a graph showing results of the first comparative example (a relationship between the sensor output Ip3 and the amount of change $\Delta Ip3$ in the sensor output at an $O_2$ concentration of 20%)

As can be understood from FIGS. 8A to 9B, NO and $NH_3$ were capable of being segregated, or stated otherwise mapping was possible, when the $O_2$ concentration was 1% and 5% (see FIGS. 8A and 8B), however, when the $O_2$ concentration exceeded 10%, as shown in FIGS. 9A and 9B, separation of NO and $NH_3$ became impossible. In the constant control of the preliminary pump voltage Vp0 shown in the first comparative example, under a high $O_2$ concentration, the preliminary adjustment chamber 21 cannot be pumped out until reaching a target oxygen concentration, and as a result, regardless of whether the preliminary pump voltage Vp0 is applied, the preliminary adjustment chamber 21 is deemed to be in the OFF state.

[Configuration of Second Gas Sensor]

Figure 11:
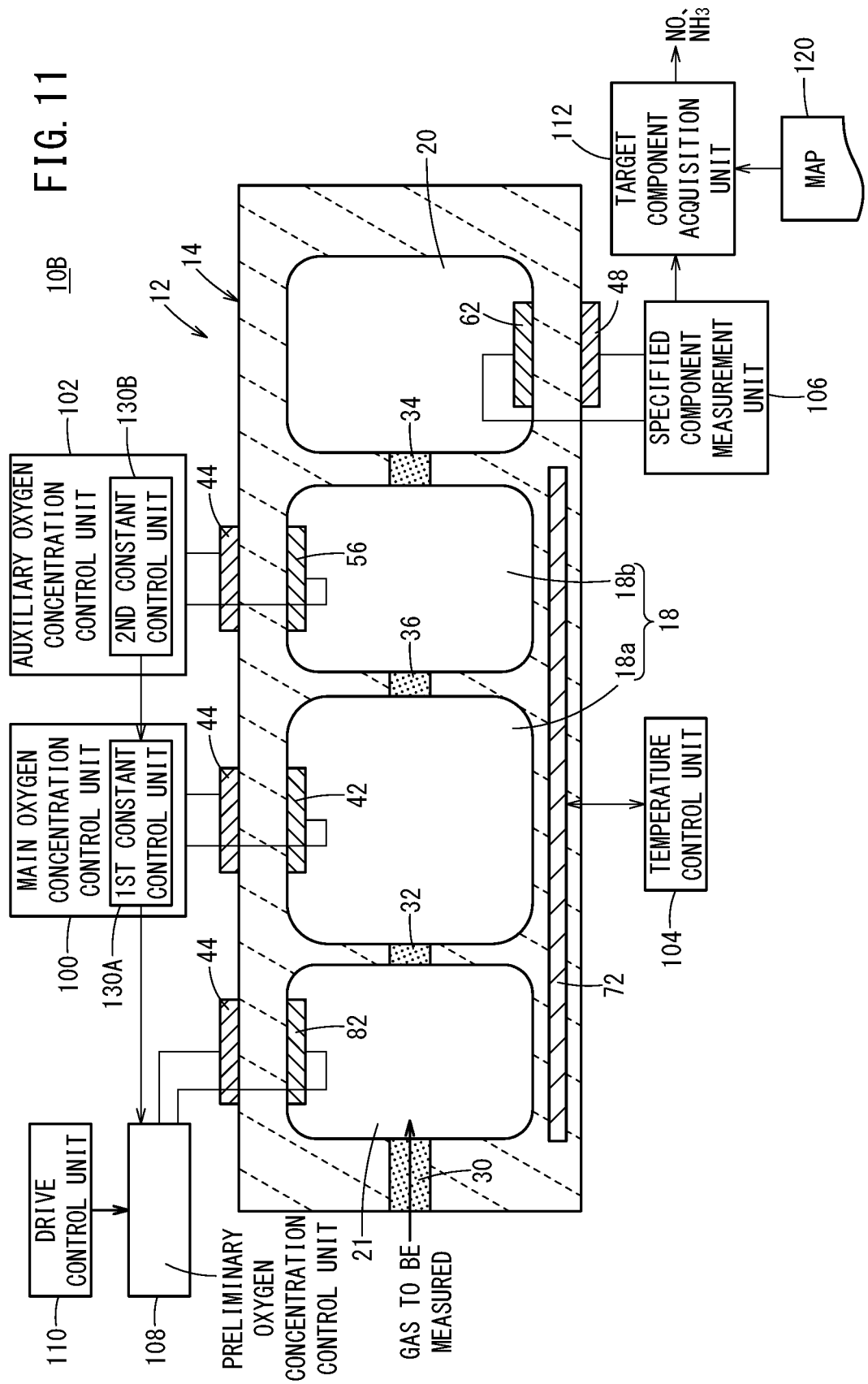
FIG. 11 is a configuration diagram schematically showing the second gas sensor.

As shown in FIGS. 10 and 11, the gas sensor according to the second embodiment (hereinafter referred to as a second gas sensor 10B) has substantially the same configuration as that of the aforementioned first gas sensor 10A (see FIGS. 1 and 2), but differs therefrom in that a second constant control unit 130B is included, in addition to the aforementioned first constant control unit 130A that controls the preliminary pump voltage Vp0 of the preliminary pump cell 80 in a manner so that the main pump current Ip1 of the main pump cell 40 becomes constant.

More specifically, as shown in FIG. 11, in the second gas sensor 10B, as described above, the main oxygen concentration control unit 100 includes the first constant control unit 130A, while in addition, the auxiliary oxygen concentration control unit 102 includes the second constant control unit 130B.

The second constant control unit 130B feedback-controls the main pump voltage Vp1 of the main pump cell 40 in a manner so that the auxiliary pump current Ip2 of the auxiliary pump cell 54 becomes constant.

In this case as well, in the same manner as the first gas sensor 10A described above, the NO concentration and the $NH_3$ concentration can be detected with high accuracy from the sensor output Ip3 and the amount of change ΔIp3 in the sensor output.

[Configuration of Third Gas Sensor]

Figure 12:
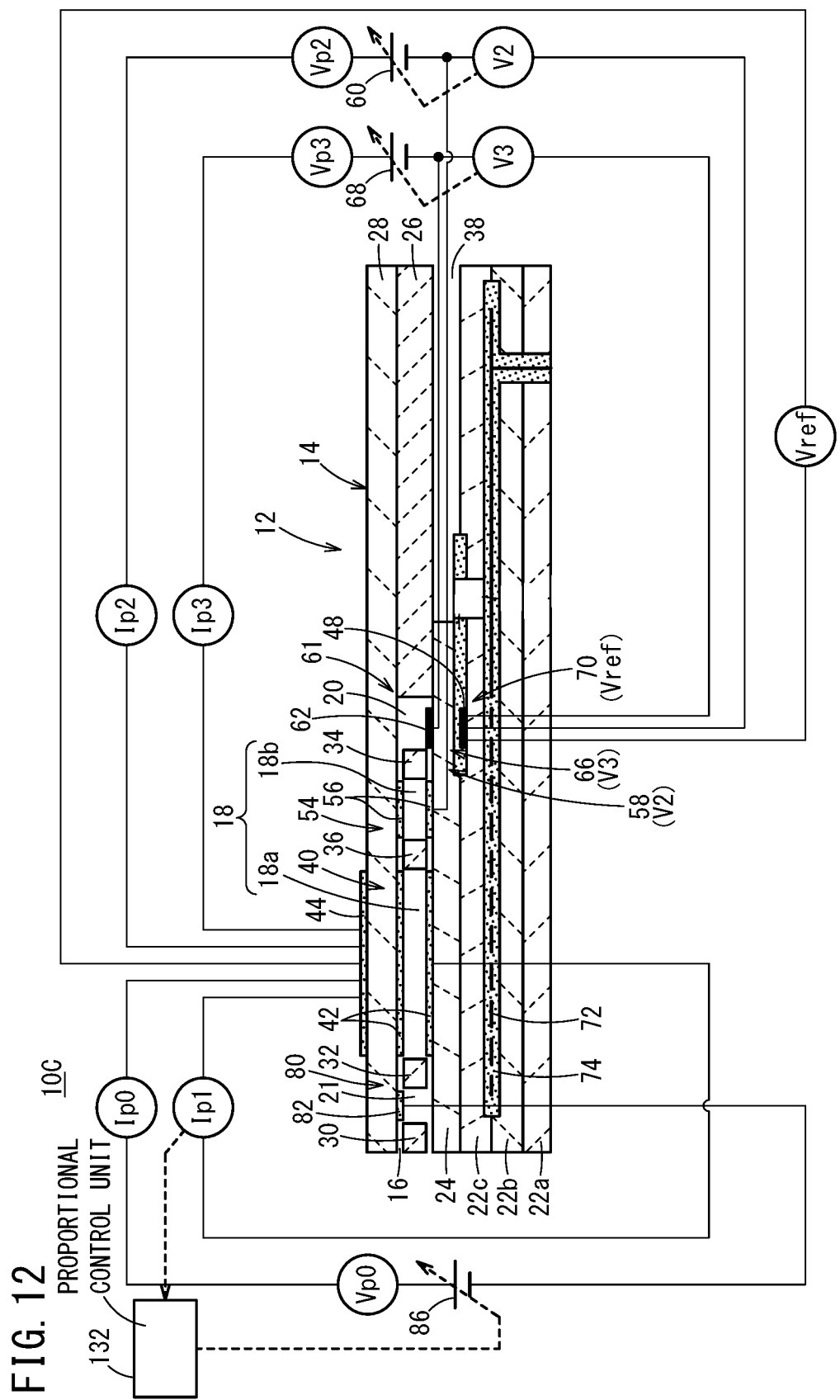
FIG. 12 is a cross-sectional view in which there is shown one structural example of a third gas sensor according to an embodiment of the present invention.
Figure 13:
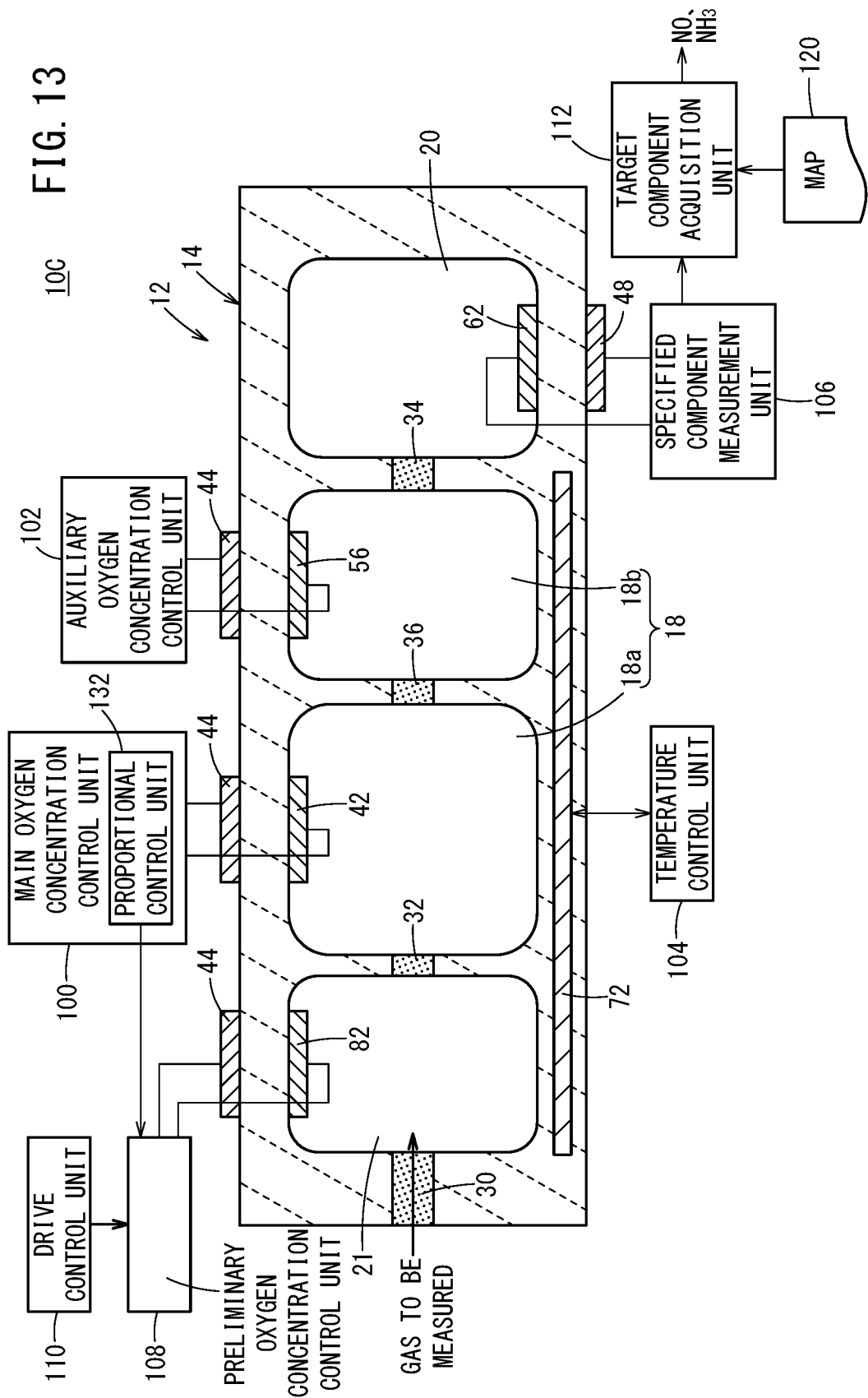
FIG. 13 is a configuration diagram schematically showing the third gas sensor.

As shown in FIGS. 12 and 13, the gas sensor according to the third embodiment (hereinafter referred to as a third gas sensor 10C) has substantially the same configuration as the aforementioned first gas sensor 10A, but differs therefrom in that a proportional control unit 132 is provided that proportionally controls the preliminary pump voltage Vp0 of the preliminary pump cell 80 with the main pump current Ip1, in a manner so that the preliminary pump voltage Vp0 of the preliminary pump cell 80 is in a proportional relationship to the main pump current Ip1 of the main pump cell 40. More specifically, as shown in FIG. 13, the main oxygen concentration control unit 100 of the third gas sensor 10C includes the proportional control unit 132.

Third Exemplary Embodiment

In the third exemplary embodiment, in the third gas sensor 10C shown in FIGS. 12 and 13, a relationship between the main pump current Ip1 and the preliminary pump voltage Vp0 in an $O_2$ concentration region (from 1 to 20%) was investigated, and the relationship between the preliminary pump current Ip0 and the preliminary pump voltage Vp0 was confirmed for each oxygen concentration.

The conditions for implementing the third exemplary embodiment were as follows.

Sensor Drive Temperature: 840° C.
Model Gases: $O_2$ and $H_2O$ (without introduction of NO and $NH_3$)
Gas Concentration: $O_2$=1 to 20%, $H_2O$=3%
Gas Flow Rate: 200 L/min (at 250° C.)

Figures 14A, 14B:
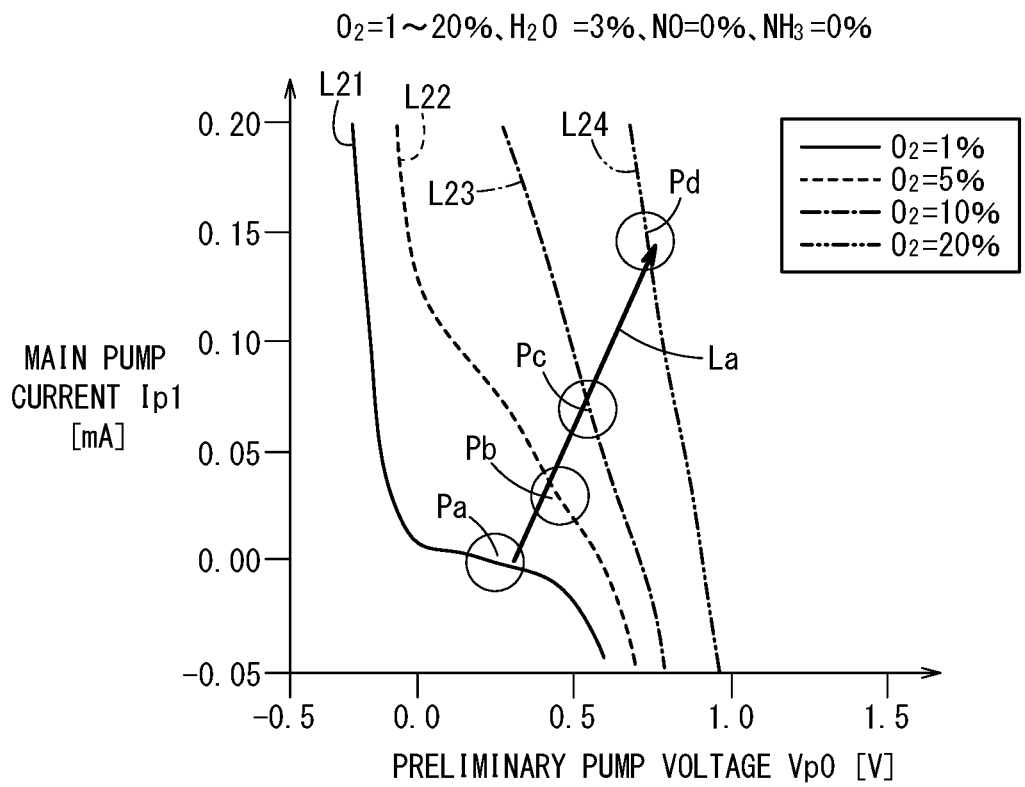
FIG. 14A is a graph showing results of a third exemplary embodiment (a relationship between a preliminary pump voltage Vp0 and a main pump current Ip1)
FIG. 14B is a table indicating results of the third exemplary embodiment (a relationship between an $O_2$ concentration and the preliminary pump voltage Vp0)
Figure 15:
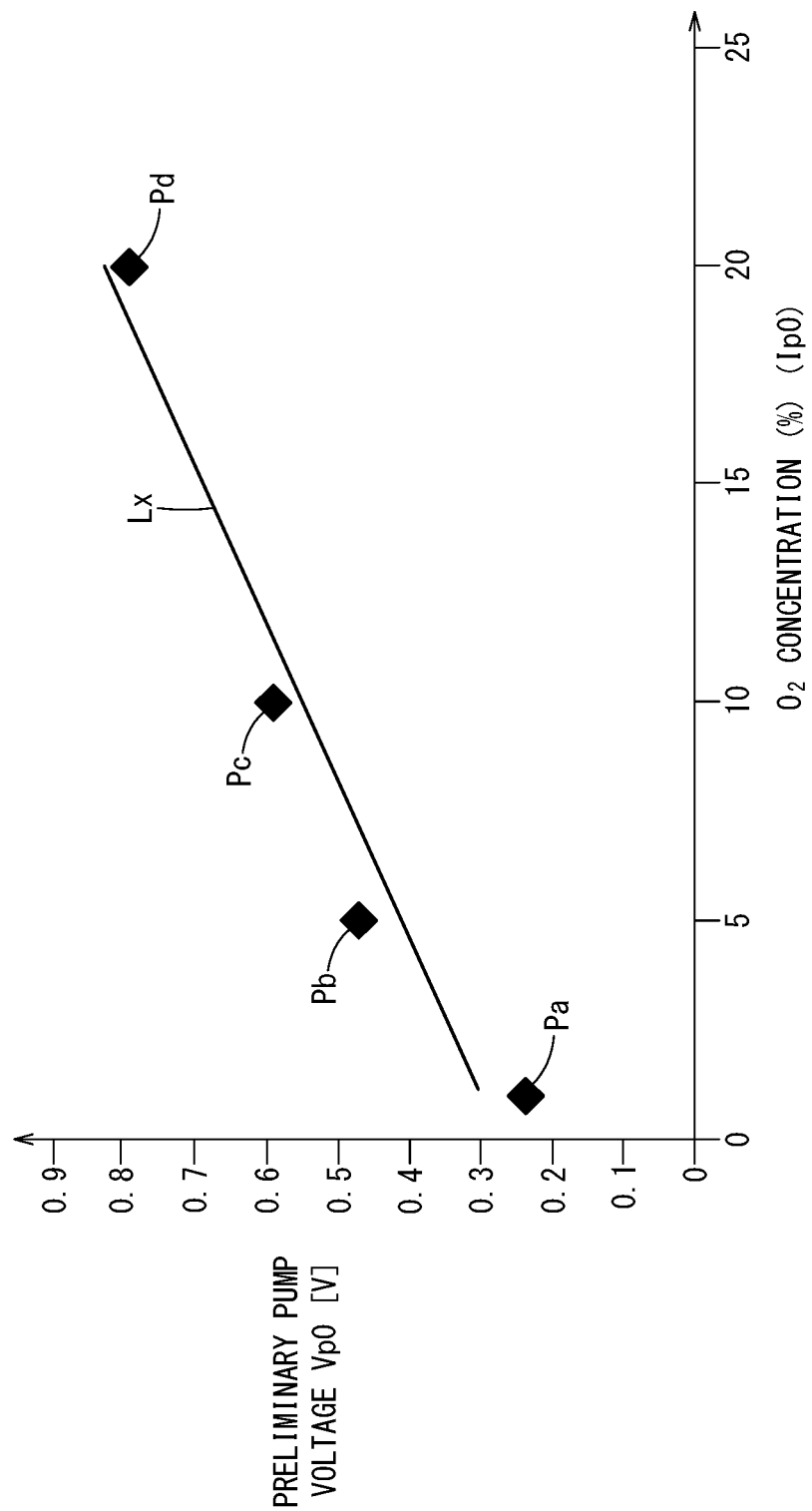
FIG. 15 is a graph showing results of the third exemplary embodiment (a relationship between an $O_2$ concentration and the preliminary pump voltage Vp0)

The measurement results are shown in the graph of FIG. 14A, the table of FIG. 14B, and the graph of FIG. 15. The graph of FIG. 14A shows a change in the main pump current Ip1 with respect to the preliminary pump voltage Vp0 (V). In the graph of FIG. 14A, a characteristic when the $O_2$ concentration is 1% is shown by the curve L21, a characteristic when the $O_2$ concentration is 5% is shown by the curve L22, a characteristic when the $O_2$ concentration is 10% is shown by the curve L23, and a characteristic when the $O_2$ concentration is 20% is shown by the curve L24.

In addition, representatively, a single straight line La rising to the right across the curves L21 to L24 is set, and respective intersection points (Pa, Pb, Pc, and Pd) are plotted. Table of FIG. 14B shows a relationship between the $O_2$ concentrations and the preliminary pump voltages Vp0 (V) corresponding to the four plotted intersection points Pa to Pd.

Furthermore, as shown in FIG. 15, the intersection points Pa to Pd were plotted on a graph having the $O_2$ concentration (%) on the horizontal axis and the preliminary pump voltage Vp0 (V) on the vertical axis, and furthermore, an approximate straight line Lx was determined therefrom using the method of least squares.

The following equation of the approximate straight line Lx was established as a proportional control equation of the preliminary pump voltage Vp0 with respect to the preliminary pump current Ip0:

$$Vp0=f(Ip0)=a \cdot Ip0+b$$

In this instance, based on the results of the graph shown in FIG. 15, a=0.0275 and b=0.2737.

Fourth Exemplary Embodiment

In the same manner as the aforementioned second exemplary embodiment, the fourth exemplary embodiment is implemented by adding NO and $NH_3$ as model gases in addition to $O_2$ and $H_2O$, and depending on the differences of the $O_2$ concentration, the NO concentration, and the $NH_3$ concentration, it is confirmed whether or not the positions of the points differ.

The conditions for implementing the fourth exemplary embodiment were as follows.

Sensor Drive Temperature: 840° C.
Model Gases: $O_2$, $H_2O$, NO, $NH_3$
Gas Concentration: $O_2$=1 to 20%, $H_2O$=3%, NO=0 to 500 ppm, $NH_3$=0 to 500 ppm
Gas Flow Rate: 200 L/min (at 250° C.)

Changes in the sensor output Ip3 in accordance with the NO concentration and the $NH_3$ concentration in a state in which driving of the preliminary pump cell 80 was turned OFF, and trends in the amount of change ΔIp3 in the sensor output due to the $NH_3$ concentration were confirmed by changing the NO concentration and the $NH_3$ concentration. The results thereof are shown in FIGS. 16A to 17B.

Figure 16A:
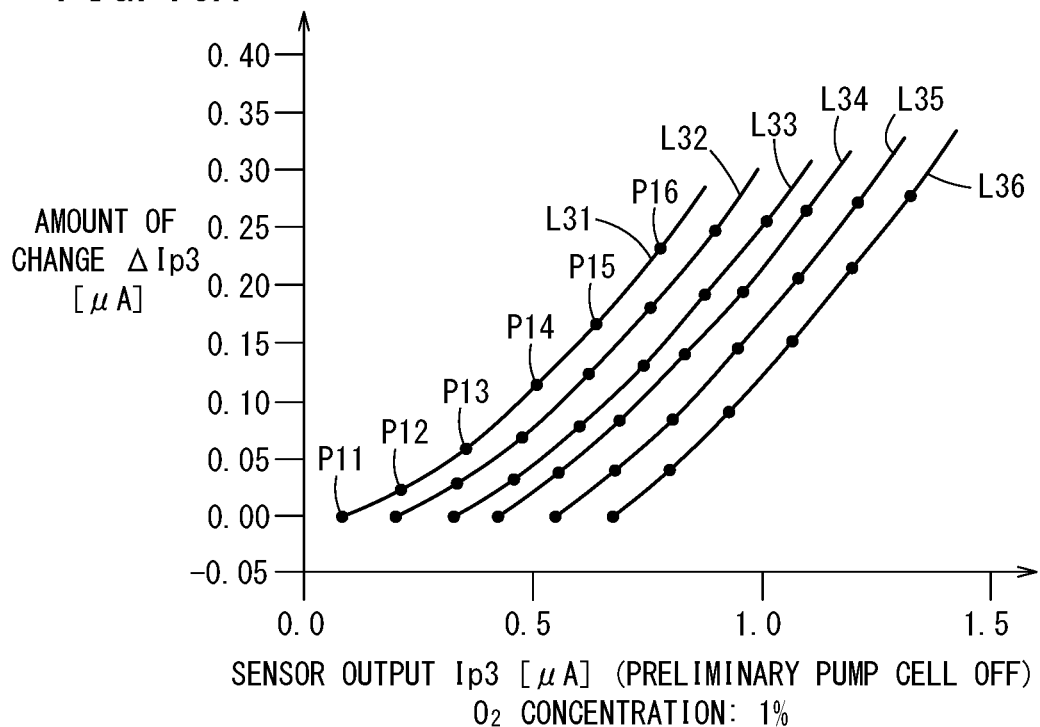
FIG. 16A is a graph showing results of a fourth exemplary embodiment (a relationship between a sensor output Ip3 and an amount of change $\Delta Ip3$ in the sensor output at an $O_2$ concentration of 1%)
Figure 16B:
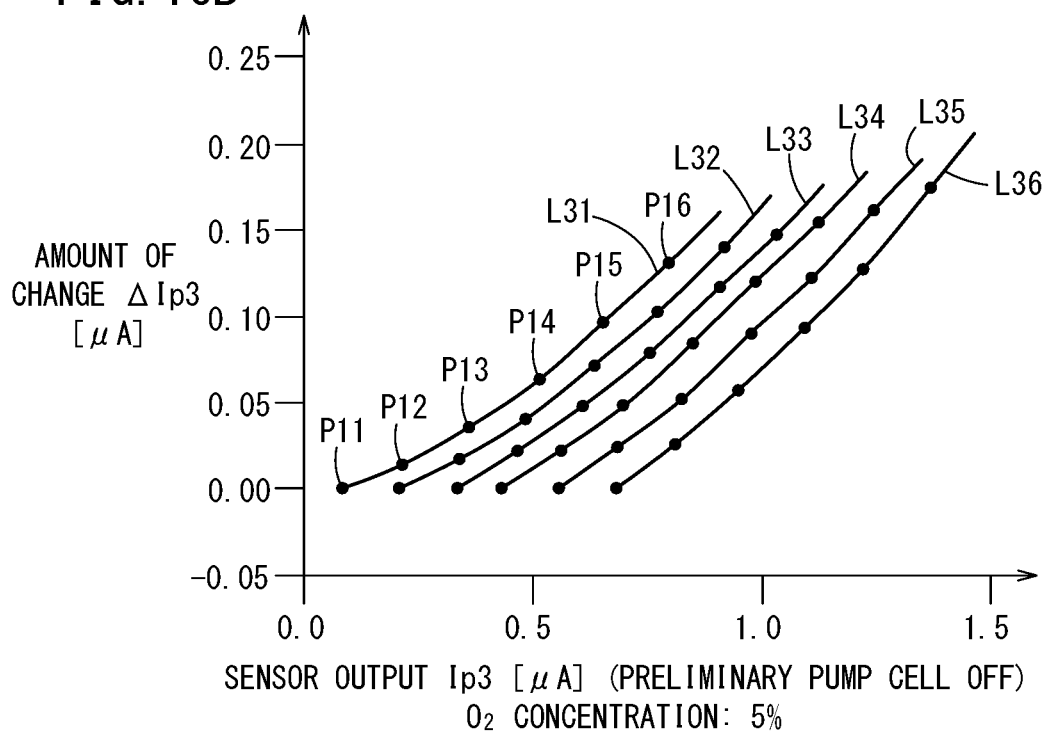
FIG. 16B is a graph showing results of the fourth exemplary embodiment (a relationship between the sensor output Ip3 and the amount of change $\Delta Ip3$ in the sensor output at an $O_2$ concentration of 5%)
Figure 17A:
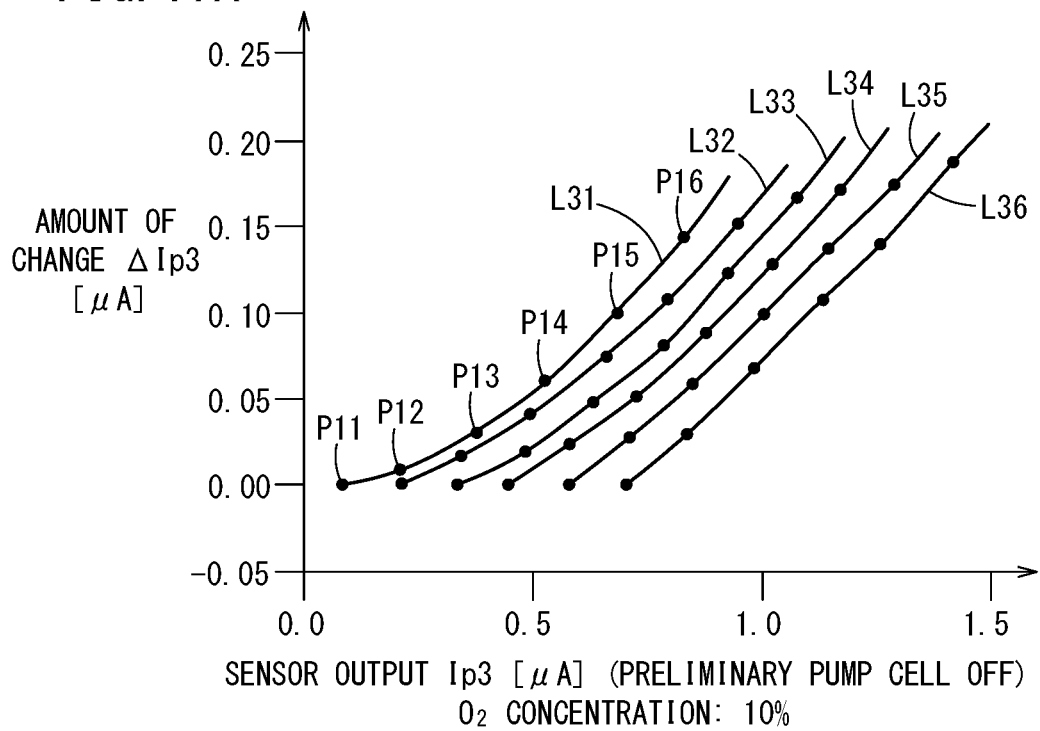
FIG. 17A is a graph showing results of the fourth exemplary embodiment (a relationship between the sensor output Ip3 and the amount of change $\Delta Ip3$ in the sensor output at an $O_2$ concentration of 10%)
Figure 17B:
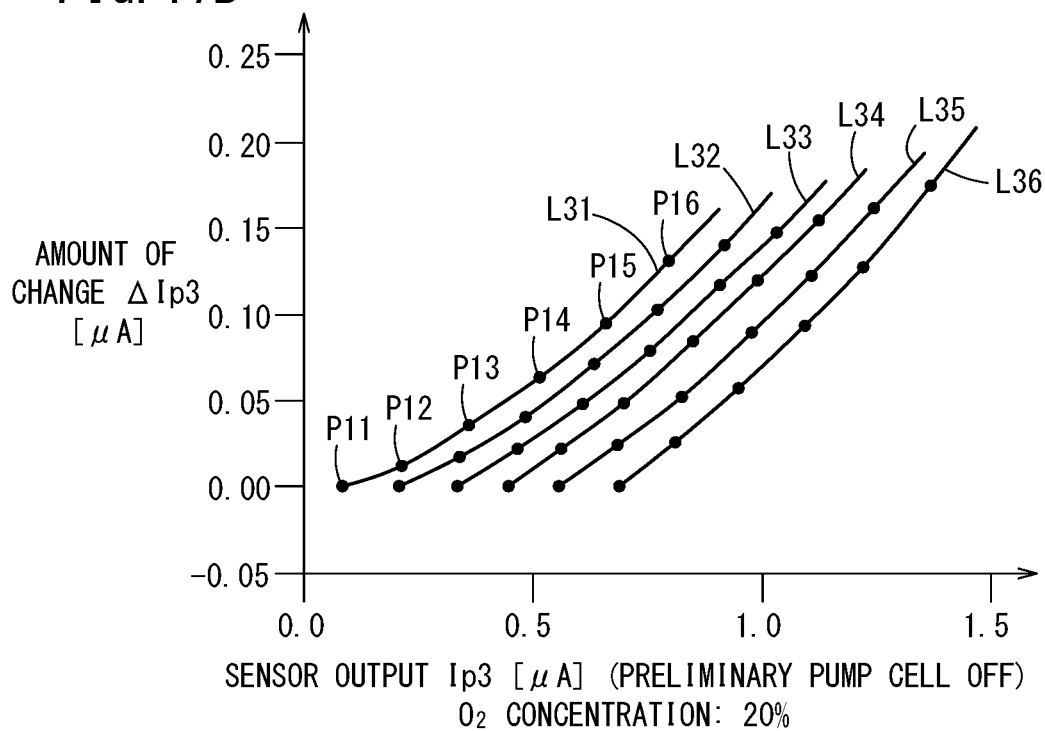
FIG. 17B is a graph showing results of the fourth exemplary embodiment (a relationship between the sensor output Ip3 and the amount of change $\Delta Ip3$ in the sensor output at an $O_2$ concentration of 20%)

FIG. 16A shows characteristics when the $O_2$ concentration is 1%, and FIG. 16B shows characteristics when the $O_2$ concentration is 5%. Further, FIG. 17A shows characteristics when the $O_2$ concentration is 10%, and FIG. 17B shows characteristics when the $O_2$ concentration is 20%.

In FIGS. 16A to 17B, a characteristic when the NO concentration is 0 ppm is shown by the curve L31, a characteristic when the NO concentration is 100 ppm is shown by the curve L32, a characteristic when the NO concentration is 200 ppm is shown by the curve L33, a characteristic when the NO concentration is 300 ppm is shown by the curve L34, a characteristic when the NO concentration is 400 ppm is shown by the curve L35, and a characteristic when the NO concentration is 500 ppm is shown by the curve L36.

Further, in FIGS. 16A to 17B, a point when the $NH_3$ concentration is 0 ppm is indicated by P11, a point when the $NH_3$ concentration is 100 ppm is indicated by P12, a point when the $NH_3$ concentration is 200 ppm is indicated by P13, a point when the $NH_3$ concentration is 300 ppm is indicated by P14, a point when the $NH_3$ concentration is 400 ppm is indicated by P15, and a point when the $NH_3$ concentration is 500 ppm is indicated by P16.

As can be understood from FIGS. 16A to 17B, since the positions of the points differ depending on the differences of the $O_2$ concentration, the NO concentration, and the $NH_3$ concentration, by mapping the relationships shown in FIGS. 16A to 17B and creating the map 120, it becomes possible to accurately detect the NO concentration and the $NH_3$ concentration from the sensor output Ip3 and the amount of change ΔIp3 in the sensor output.

Fifth Exemplary Embodiment

In the fifth exemplary embodiment, the third gas sensor 10C shown in FIGS. 12 and 13 was used. The main pump current Ip1 when the preliminary pump cell 80 is turned OFF is directly proportional to the $O_2$ concentration. Accordingly, the concentration of $O_2$ within the exhaust gas is grasped from the preliminary pump current Ip0 at the time that the preliminary pump cell 80 is OFF, and a setting point for the preliminary pump voltage Vp0 at the time that the preliminary pump cell 80 is turned ON is subsequently determined from the preliminary pump current Ip0 (when OFF).

For example, as shown in the graph of FIG. 18, the characteristics of the main pump current Ip1 with respect to the $O_2$ concentration (when the preliminary pump cell is OFF) are prepared in advance as a map, and using the map, the $O_2$ concentration can be determined from the main pump current Ip1 when OFF. In addition, based on the grasped $O_2$ concentration, the preliminary pump voltage Vp0 is determined, for example, from the table shown in FIG. 14B.

Sixth Exemplary Embodiment

Figure 19:
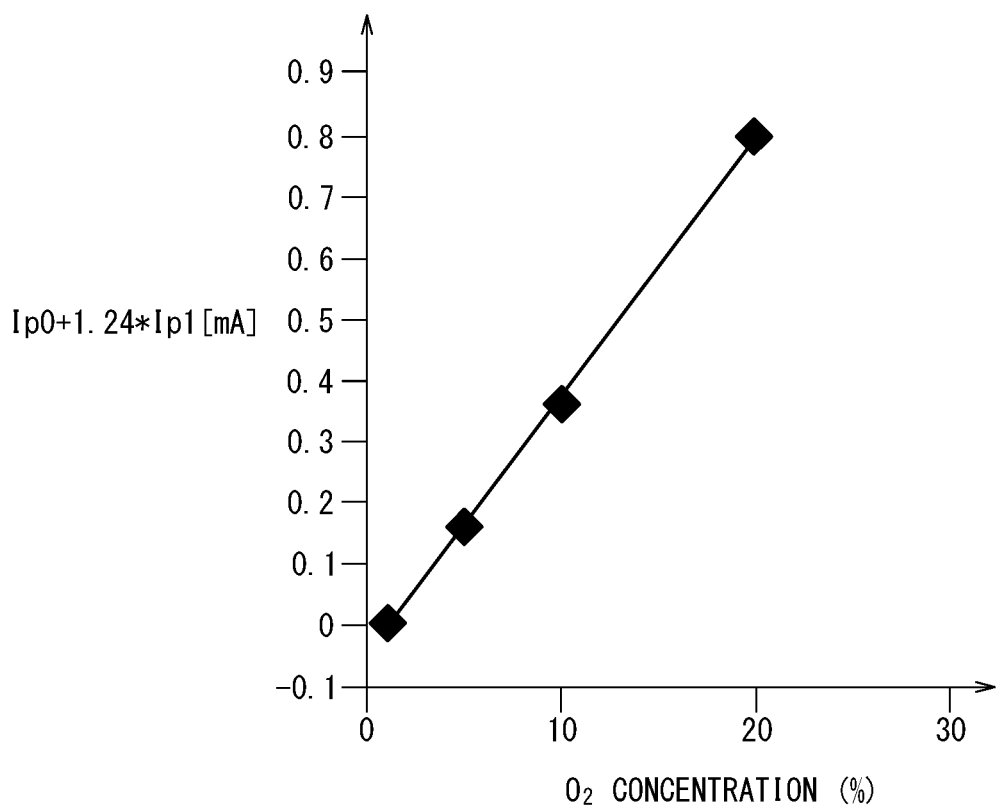
FIG. 19 is a graph showing results of the sixth exemplary embodiment ($O_2$ concentration=Ip0+1.24×Ip1)

In the sixth exemplary embodiment, in the same manner, the third gas sensor 10C shown in FIGS. 12 and 13 was used. The preliminary pump current Ip0 when the preliminary pump cell 80 is turned ON represents the amount of oxygen that is pumped in and out of the preliminary pump cell 80, and the main pump current Ip1 represents the amount of oxygen that is pumped in and out of the main adjustment chamber 18a (oxygen concentration adjustment chamber 18). More specifically, the total amount of oxygen that is pumped in and out of the third gas sensor 10C is represented by the preliminary pump current Ip0+the main pump current Ip1, and such an amount is equivalent to the $O_2$ concentration of the exhaust gas. Stated otherwise, regardless of the value that the preliminary pump voltage Vp0 becomes when the preliminary pump cell 80 is turned ON, the following equation:

$$O_2 \text{ concentration} = Ip0 + a \times Ip1 \text{ (}a \text{ is a constant greater than 1),}$$

is satisfied, and the coefficient "a" is a value determined by the magnitudes of the diffusion resistance D0 of the first diffusion rate control member 30 and the diffusion resistance D1 of the second diffusion rate control member 32. Due to the diffusion resistances D0 and D1, the amount of oxygen attained by diffusion decreases as it progresses inside. Further, the value of the coefficient "a" depends on the design values of the diffusion resistances D0 and D1. For example, in the case that the coefficient "a" is 1.24, the graph as shown in FIG. 19 is created. The $O_2$ concentration can be calculated from such a graph. In addition, if the $O_2$ concentration is ascertained, the preliminary pump voltage Vp0 may be determined from the table shown in FIG. 14B.

[Configuration of Fourth Gas Sensor]

Figure 20:
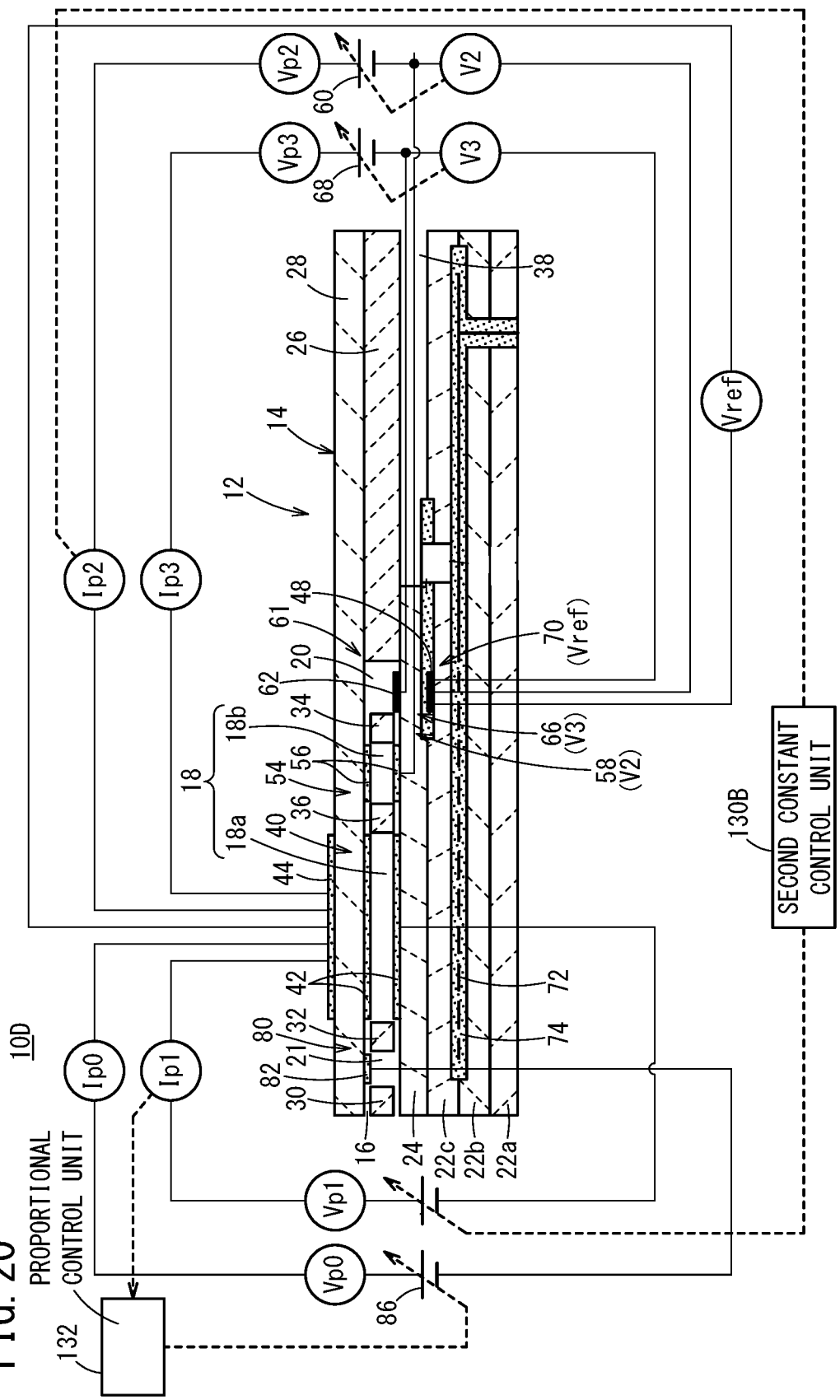
FIG. 20 is a cross-sectional view in which there is shown one structural example of a fourth gas sensor according to an embodiment of the present invention.

As shown in FIG. 20, the gas sensor according to the fourth embodiment (hereinafter referred to as a fourth gas sensor 10D) has substantially the same configuration as that of the aforementioned third gas sensor 10C (see FIGS. 12 and 13), but differs therefrom in that, similar to the aforementioned second gas sensor 10B (see FIG. 10), the second constant control unit 130B is included.

The second constant control unit 130B feedback-controls the main pump voltage Vp1 of the main pump cell 40 in a manner so that the auxiliary pump current Ip2 of the auxiliary pump cell 54 becomes constant.

In this case as well, in the same manner as the third gas sensor 10C described above, the NO concentration and the $NH_3$ concentration can be detected with high accuracy from the sensor output Ip3 and the amount of change ΔIp3 in the sensor output.

The gas sensor and the method of controlling the gas sensor according to the present invention are not limited to the embodiments described above, and it is a matter of course that various configurations could be adopted therein without departing from the essence and gist of the present invention.

In the examples described above, examples were illustrated in which $NH_3$ as the second target component is converted into NO inside the preliminary adjustment chamber 21 at a conversion ratio of 100%. However, the conversion ratio of $NH_3$ need not necessarily be 100%, and the conversion ratio can be set arbitrarily, within a range in which a correlation with good reproducibility with the $NH_3$ concentration within the gas to be measured is obtained.

Further, driving of the preliminary oxygen concentration control unit 108 may be performed in a direction of pumping oxygen out from the interior of the preliminary adjustment chamber 21, or in a direction of pumping oxygen into the preliminary adjustment chamber 21, and it is sufficient insofar as the measured pump current Ip3, which is the output of the measurement pump cell 61, changes with good reproducibility due to the presence of $NH_3$ that serves as the second target component.

In practicing the present invention, various configurations for improving reliability may be added as components for an automobile to such an extent that the concept of the present invention is not impaired.

What is claimed is:
1. A gas sensor comprising:
   a sensor element including a structural body made up from a solid electrolyte that exhibits at least oxygen ion conductivity, a gas introduction port formed in the structural body and into which a gas to be measured is introduced, a main oxygen concentration adjustment chamber communicating with the gas introduction port, an auxiliary oxygen concentration adjustment chamber communicating with the main oxygen concentration adjustment chamber, a measurement chamber communicating with the auxiliary oxygen concentration adjustment chamber, and a preliminary adjustment chamber disposed between the gas introduction port and the main oxygen concentration adjustment chamber, and communicating with the gas introduction port;
   a main oxygen concentration control unit configured to control an oxygen concentration inside the main oxygen concentration adjustment chamber;
   an auxiliary oxygen concentration control unit configured to control the oxygen concentration inside the auxiliary oxygen concentration adjustment chamber;
   a temperature control unit configured to control a temperature of the sensor element;
   a specified component measurement unit configured to measure a concentration of a specified component inside the measurement chamber;
   electrodes formed on an inner surface and an outer surface of the solid electrolyte;

a preliminary oxygen concentration control unit configured to control the oxygen concentration inside the preliminary adjustment chamber;

a drive control unit configured to control the preliminary oxygen concentration control unit; and a target component acquisition unit configured to acquire concentrations of a first target component and a second target component, based on a difference between a sensor output from the specified component measurement unit at a time of a first operation of the preliminary oxygen concentration control unit, and a sensor output from the specified component measurement unit at a time of a second operation of the preliminary oxygen concentration control unit, and one of the sensor outputs, wherein the main oxygen concentration control unit includes a main pump cell configured to pump oxygen inside the main oxygen concentration adjustment chamber, by applying a main pump voltage between a main interior side electrode formed in the main oxygen concentration adjustment chamber and an exterior side electrode formed on an outer side of the structural body, and causing a main pump current to flow between the main interior side electrode and the exterior side electrode, wherein the preliminary oxygen concentration control unit includes a preliminary pump cell configured to pump the oxygen inside the preliminary adjustment chamber, by applying a preliminary pump voltage between an interior side preliminary electrode formed in the preliminary adjustment chamber and the exterior side electrode formed on the outer side of the structural body, and causing a preliminary pump current to flow between the interior side preliminary electrode and the exterior side electrode, and wherein the main oxygen concentration control unit includes a constant control unit configured to control the preliminary pump voltage of the preliminary pump cell in a manner so that the main pump current of the main pump cell becomes constant.

2. The gas sensor according to claim 1, wherein:

the auxiliary oxygen concentration control unit includes an auxiliary pump cell configured to pump the oxygen inside the auxiliary oxygen concentration adjustment chamber, by applying an auxiliary pump voltage between an auxiliary interior side electrode formed in the auxiliary oxygen concentration adjustment chamber and the exterior side electrode formed on the outer side of the structural body, and causing an auxiliary pump current to flow between the auxiliary interior side electrode and the exterior side electrode; and the auxiliary oxygen concentration control unit includes a constant control unit configured to control the main pump voltage of the main pump cell in a manner so that the auxiliary pump current of the auxiliary pump cell becomes constant.

3. A gas sensor comprising:

a sensor element including a structural body made up from a solid electrolyte that exhibits at least oxygen ion conductivity, a gas introduction port formed in the structural body and into which a gas to be measured is introduced, a main oxygen concentration adjustment chamber communicating with the gas introduction port, an auxiliary oxygen concentration adjustment chamber communicating with the main oxygen concentration adjustment chamber, a measurement chamber communicating with the auxiliary oxygen concentration adjustment chamber, and a preliminary adjustment chamber disposed between the gas introduction port and the main oxygen concentration adjustment chamber, and communicating with the gas introduction port;

a main oxygen concentration control unit configured to control an oxygen concentration inside the main oxygen concentration adjustment chamber;

an auxiliary oxygen concentration control unit configured to control the oxygen concentration inside the auxiliary oxygen concentration adjustment chamber;

a temperature control unit configured to control a temperature of the sensor element;

a specified component measurement unit configured to measure a concentration of a specified component inside the measurement chamber;

electrodes formed on an inner surface and an outer surface of the solid electrolyte;

a preliminary oxygen concentration control unit configured to control the oxygen concentration inside the preliminary adjustment chamber;

a drive control unit configured to control the preliminary oxygen concentration control unit; and a target component acquisition unit configured to acquire concentrations of a first target component and a second target component, based on a difference between a sensor output from the specified component measurement unit at a time of a first operation of the preliminary oxygen concentration control unit, and a sensor output from the specified component measurement unit at a time of a second operation of the preliminary oxygen concentration control unit, and one of the sensor outputs, wherein the main oxygen concentration control unit includes a main pump cell configured to pump oxygen inside the main oxygen concentration adjustment chamber, by applying a main pump voltage between a main interior side electrode formed in the main oxygen concentration adjustment chamber and an exterior side electrode formed on an outer side of the structural body, and causing a main pump current to flow between the main interior side electrode and the exterior side electrode, wherein the preliminary oxygen concentration control unit includes a preliminary pump cell configured to pump the oxygen inside the preliminary adjustment chamber, by applying a preliminary pump voltage between an interior side preliminary electrode formed in the preliminary adjustment chamber and the exterior side electrode formed on the outer side of the structural body, and causing a preliminary pump current to flow between the interior side preliminary electrode and the exterior side electrode, and wherein the main oxygen concentration control unit includes a proportional control unit configured to proportionally control the preliminary pump voltage of the preliminary pump cell based on the main pump current of the main pump cell.

4. The gas sensor according to claim 3, wherein the preliminary pump voltage is obtained based on $O_2$ concentration, the $O_2$ concentration being determined by the following arithmetic equation:

$$O_2 \text{ concentration} = Ip0 + a \times Ip1, \text{ and}$$

wherein a is a constant greater than 1, the preliminary pump current is defined by $Ip0$, and the main pump current is defined by $Ip1$.

5. The gas sensor according to claim 3, wherein:
the auxiliary oxygen concentration control unit includes an auxiliary pump cell configured to pump the oxygen inside the auxiliary oxygen concentration adjustment chamber, by applying an auxiliary pump voltage between an auxiliary interior side electrode formed in the auxiliary oxygen concentration adjustment chamber and the exterior side electrode formed on the outer side of the structural body, and causing an auxiliary pump current to flow between the auxiliary interior side electrode and the exterior side electrode; and
the auxiliary oxygen concentration control unit includes a constant control unit configured to control the main pump voltage of the main pump cell in a manner so that the auxiliary pump current of the auxiliary pump cell becomes constant.

6. A gas sensor comprising:
a sensor element including a structural body made up from a solid electrolyte that exhibits at least oxygen ion conductivity, a gas introduction port formed in the structural body and into which a gas to be measured is introduced, a main oxygen concentration adjustment chamber communicating with the gas introduction port, an auxiliary oxygen concentration adjustment chamber communicating with the main oxygen concentration adjustment chamber, a measurement chamber communicating with the auxiliary oxygen concentration adjustment chamber, and a preliminary adjustment chamber disposed between the gas introduction port and the main oxygen concentration adjustment chamber, and communicating with the gas introduction port;
a main oxygen concentration control unit configured to control an oxygen concentration inside the main oxygen concentration adjustment chamber;
an auxiliary oxygen concentration control unit configured to control the oxygen concentration inside the auxiliary oxygen concentration adjustment chamber;
a specified component measurement unit configured to measure a concentration of a specified component inside the measurement chamber;
electrodes formed on an inner surface and an outer surface of the solid electrolyte;
a preliminary oxygen concentration control unit configured to control the oxygen concentration inside the preliminary adjustment chamber; and
at least one processor, which when executing at least one program, configures the at least one processor to:
control a temperature of the sensor element;
control the preliminary oxygen concentration control unit; and
acquire concentrations of a first target component and a second target component, based on a difference between a sensor output from the specified component measurement unit at a time of a first operation of the preliminary oxygen concentration control unit, and a sensor output from the specified component measurement unit at a time of a second operation of the preliminary oxygen concentration control unit, and one of the sensor outputs,
wherein the main oxygen concentration control unit includes a main pump cell configured to pump oxygen inside the main oxygen concentration adjustment chamber, by applying a main pump voltage between a main interior side electrode formed in the main oxygen concentration adjustment chamber and an exterior side electrode formed on an outer side of the structural body, and causing a main pump current to flow between the main interior side electrode and the exterior side electrode,
wherein the preliminary oxygen concentration control unit includes a preliminary pump cell configured to pump the oxygen inside the preliminary adjustment chamber, by applying a preliminary pump voltage between an interior side preliminary electrode formed in the preliminary adjustment chamber and the exterior side electrode formed on the outer side of the structural body, and causing a preliminary pump current to flow between the interior side preliminary electrode and the exterior side electrode, and
wherein the at least one processor is further configured to control the preliminary pump voltage of the preliminary pump cell in a manner so that the main pump current of the main pump cell becomes constant.

7. The gas sensor according to claim 6, wherein:
the auxiliary oxygen concentration control unit includes an auxiliary pump cell configured to pump the oxygen inside the auxiliary oxygen concentration adjustment chamber, by applying an auxiliary pump voltage between an auxiliary interior side electrode formed in the auxiliary oxygen concentration adjustment chamber and the exterior side electrode formed on the outer side of the structural body, and causing an auxiliary pump current to flow between the auxiliary interior side electrode and the exterior side electrode; and
the at least one processor is further configured to control the main pump voltage of the main pump cell in a manner so that the auxiliary pump current of the auxiliary pump cell becomes constant.

8. A gas sensor comprising:
a sensor element including a structural body made up from a solid electrolyte that exhibits at least oxygen ion conductivity, a gas introduction port formed in the structural body and into which a gas to be measured is introduced, a main oxygen concentration adjustment chamber communicating with the gas introduction port, an auxiliary oxygen concentration adjustment chamber communicating with the main oxygen concentration adjustment chamber, a measurement chamber communicating with the auxiliary oxygen concentration adjustment chamber, and a preliminary adjustment chamber disposed between the gas introduction port and the main oxygen concentration adjustment chamber, and communicating with the gas introduction port;
a main oxygen concentration control unit configured to control an oxygen concentration inside the main oxygen concentration adjustment chamber;
an auxiliary oxygen concentration control unit configured to control the oxygen concentration inside the auxiliary oxygen concentration adjustment chamber;
a specified component measurement unit configured to measure a concentration of a specified component inside the measurement chamber;
electrodes formed on an inner surface and an outer surface of the solid electrolyte;
a preliminary oxygen concentration control unit configured to control the oxygen concentration inside the preliminary adjustment chamber; and
at least one processor, which when executing at least one program, configures the at least one processor to:
control a temperature of the sensor element;
control the preliminary oxygen concentration control unit; and acquire concentrations of a first target component and a second target component, based on a difference between a sensor output from the specified component measurement unit at a time of a first operation of the preliminary oxygen concentration control unit, and a sensor output from the specified component measurement unit at a time of a second operation of the preliminary oxygen concentration control unit, and one of the sensor outputs, wherein the main oxygen concentration control unit includes a main pump cell configured to pump oxygen inside the main oxygen concentration adjustment chamber, by applying a main pump voltage between a main interior side electrode formed in the main oxygen concentration adjustment chamber and an exterior side electrode formed on an outer side of the structural body, and causing a main pump current to flow between the main interior side electrode and the exterior side electrode, wherein the preliminary oxygen concentration control unit includes a preliminary pump cell configured to pump the oxygen inside the preliminary adjustment chamber, by applying a preliminary pump voltage between an interior side preliminary electrode formed in the preliminary adjustment chamber and the exterior side electrode formed on the outer side of the structural body, and causing a preliminary pump current to flow between the interior side preliminary electrode and the exterior side electrode, and wherein the at least one processor is further configured to proportionally control the preliminary pump voltage of the preliminary pump cell based on the main pump current of the main pump cell.

9. The gas sensor according to claim 8, wherein the preliminary pump voltage is obtained based on $O_2$ concentration, the $O_2$ concentration being determined by the following arithmetic equation:

$$O_2\text{ concentration}=Ip0+a{\times}Ip1, \text{ and}$$

wherein a is a constant greater than 1, the preliminary pump current is defined by $Ip0$, and the main pump current is defined by $Ip1$.

10. The gas sensor according to claim 8, wherein:

the auxiliary oxygen concentration control unit includes an auxiliary pump cell configured to pump the oxygen inside the auxiliary oxygen concentration adjustment chamber, by applying an auxiliary pump voltage between an auxiliary interior side electrode formed in the auxiliary oxygen concentration adjustment chamber and the exterior side electrode formed on the outer side of the structural body, and causing an auxiliary pump current to flow between the auxiliary interior side electrode and the exterior side electrode; and the at least one processor is further configured to control the main pump voltage of the main pump cell in a manner so that the auxiliary pump current of the auxiliary pump cell becomes constant.

\* \* \* \* \*